United States Patent [19]

King et al.

[11] Patent Number: 4,902,658

[45] Date of Patent: Feb. 20, 1990

[54] ALKOXYLATION USING HETEROGENEOUS CALCIUM CATALYSTS AND PRODUCTS THEREFROM

[75] Inventors: Stephen W. King, Scott Depot; Robert J. Knopf, St. Albans, both of W. Va.

[73] Assignee: Union Carbide Corporation, Danbury, Conn.

[21] Appl. No.: 102,939

[22] Filed: Sep. 30, 1987

[51] Int. Cl.$^4$ ............................................. B01J 31/06
[52] U.S. Cl. .................................... 502/159; 252/351; 568/619
[58] Field of Search ............... 502/159, 162, 167, 168, 502/171, 172

[56] References Cited

U.S. PATENT DOCUMENTS

| | | | |
|---|---|---|---|
| 2,934,505 | 4/1960 | Gurgiolo | 260/2 |
| 3,256,211 | 6/1966 | Bailey et al. | 502/171 X |
| 3,328,306 | 6/1967 | Ellis | 252/99 |
| 3,682,849 | 8/1972 | Smith et al. | 260/615 B |
| 4,098,818 | 7/1978 | Krummel et al. | 260/535 R |
| 4,210,764 | 7/1980 | Yang et al. | 568/618 |
| 4,223,164 | 9/1980 | Yang et al. | 568/618 |
| 4,239,917 | 12/1980 | Yang | 568/618 |
| 4,254,287 | 3/1981 | Ziegenhain et al. | 568/621 |
| 4,282,387 | 8/1981 | Olstowski et al. | 568/618 |
| 4,302,613 | 11/1981 | Yang et al. | 568/618 |
| 4,306,093 | 12/1981 | Yang et al. | 568/618 |
| 4,323,698 | 4/1982 | Haag et al. | 502/159 X |
| 4,359,589 | 11/1982 | Brownscombe | 568/618 |
| 4,396,779 | 8/1983 | Edwards | 568/618 |
| 4,396,780 | 8/1983 | Shtykh et al. | 568/620 |
| 4,453,022 | 6/1984 | McCain et al. | 568/618 |
| 4,453,023 | 6/1984 | McCain | 568/618 |
| 4,659,778 | 4/1987 | Williams | 525/107 |
| 4,714,691 | 12/1987 | Goins et al. | 502/159 X |

FOREIGN PATENT DOCUMENTS

| | | |
|---|---|---|
| 0026544 | 4/1981 | European Pat. Off. . |
| 0026546 | 4/1981 | European Pat. Off. . |
| 0026547 | 4/1981 | European Pat. Off. . |
| 0095562 | 12/1983 | European Pat. Off. . |
| 1462133 | 1/1977 | United Kingdom . |
| 1462134 | 1/1977 | United Kingdom . |

OTHER PUBLICATIONS

Kochurovskaya, G. G. et al., Kriobiol. Kriomed., 3, 1977, pp. 76–79.
Turova, N. Y. et al., Chemical News, Uspekhi Khimii, Mar. 1965, pp. 161–185.
U.S. patent application Ser. No. 454,560, filed Dec. 30, 1982.
Schick, Martin J., Nonionic Surfactants, Marcel Dekker, Inc., New York, pp. 8–43, (1967).
U.S. patent application Ser. No. 621,991, filed Jun. 22, 1984.

Primary Examiner—Patrick P. Garvin
Attorney, Agent, or Firm—Gerald L. Coon

[57] ABSTRACT

This invention relates to heterogeneous (organic polymer-supported) calcium-containing catalysts and the use thereof in the preparation of alkoxylation products, i.e., condensation reaction products of alkylene oxides and organic compounds having at least one active hydrogen. In another aspect of this invention, processes are provided for preparing heterogeneous (organic polymer-supported) calcium-containing catalysts for alkoxylation using calcium oxide or calcium hydroxide as sources for the catalytically-active calcium. In a further aspect of this invention, alkoxylation products are provided that have beneficial, narrow molecular weight ranges and are essentially neutral in pH and free from catalyst residues.

25 Claims, 5 Drawing Sheets

ALKOXYLATION USING HETEROGENEOUS CALCIUM CATALYSTS AND PRODUCTS THEREFROM

BRIEF SUMMARY OF THE INVENTION

1. Technical Field

This invention relates to heterogeneous (organic polymer-supported) calcium-containing catalysts and the use thereof in the preparation of alkoxylation products, i.e., condensation reaction products of alkylene oxides and organic compounds having at least one active hydrogen. In another aspect of the invention, processes are provided for preparing heterogeneous (organic polymer-supported) calcium-containing catalysts for alkoxylation using calcium oxide or calcium hydroxide as sources for the catalytically-active calcium. In a further aspect of the invention, alkoxylation products are provided that have beneficial, narrow molecular weight ranges and are essentially neutral in pH and free from catalyst residues. These alkoxylation products can be prepared using heterogeneous, modified calcium-containing catalysts.

2. Background of the Invention

A variety of products such as surfactants, functional fluids, glycol ethers, polyols, and the like, are commercially prepared by the condensation reaction of alkylene oxides with organic compounds having at least one active hydrogen, generally, in the presence of an alkaline or acidic catalyst. The types and properties of the alkoxylation products depend on, among other things, the active hydrogen compound, the alkylene oxide, and the mole ratio of alkylene oxide to organic compound employed, as well as the catalyst. As a result of the alkoxylation, a mixture of condensation product species are obtained having a range of molecular weights.

In many applications of alkoxylated products, certain of the alkoxylation species provide much greater activity than others. Consequently, alkoxylation processes are desired that are selective to the production of those alkoxylation species. Further, for many of these uses, mixtures of alkoxylation products falling within a narrow range of molecular distribution of reacted alkylene oxide are believed to be superior to alkoxylation products in which a single alkoxylation specie predominates. For example, in a surfactant composition the range of materials on which the surfactant will be required to operate will normally vary. A range of alkoxylation species, even though narrow, will enhance the performance of the surfactant to the variety of materials which it may encounter. Further, mixtures of closely related alkoxylation species can provide a mixture having other improved properties such as in respect to cloud point, freezing point, pour point and viscosity as compared to a single specie. There, however, is a balance, and if the distribution of species becomes too broad, not only are less desirable alkoxylation species diluting the mixture, but also the more hydrophilic or lipophilic components than those in the sought range can be detrimental to the sought properties.

Moreover, a wide range of alkoxylation species can restrict the flexibility in ultimate product formulation using the alkoxylation reaction product. For example, in making oil-in-water emulsion products it is often desired to prepare a concentrated composition that minimizes the weight percent of water. This concentrate may then be diluted with water at the time of use, thereby saving the expense of shipping and storing water. The ability to form a desirable concentrate is generally dependent, in part, on having a narrow distribution of alkoxylation species since if heavier moieties are present, a reactor portion of water is usually required otherwise gelling (evidencing product instability) may occur.

The recognition that certain distributions of moles of alkylene oxide to moles of organic compound in alkoxylation products can be important has long been recognized. For example, British Patent Specification No. 1,399,966 discloses the use of ethoxylates having a hydrophilic-lipophilic balance (HLB) of from about 10 to about 13.5 for use in a laundry detergent. In order to provide this HLB, the moles of ethylene oxide reacted per mole of fatty alcohol is described as being critical. In British Patent Specification No. 1,462,133, the sought cleaning composition employed alkylene oxide cosurfactants sufficient to provide even a narrower HLB, i.e., from about 10 to about 12.5. In British Specification No. 1,462,134, a detergent composition is disclosed which uses ethoxylates having an HLB of from about 9.5 to 11.5, with the preferred ethoxylates having an HLB of 10.0 to 11.1.

Thus, with the increased understanding of the properties to be provided by an alkoxylation product, greater demands are placed on tailoring the manufacture of the alkoxylation product to enhance the sought properties. Accordingly, efforts have been expended to provide alkoxylated products in which the distribution of reacted alkylene oxide units per mole of organic compound is limited to a range in which the sought properties are enhanced.

Alkoxylation processes are characterized by the condensation reaction in the presence of a catalyst of at least one alkylene oxide with at least one organic compound containing at least one active hydrogen. Perhaps the most common catalyst is potassium hydroxide. The products made using potassium hydroxide, however, generally exhibit a broad distribution of alkoxylate species. See, for example, M. J. Schick, *Nonionic Surfactants*, Volume 1, Marcel Dekker, Inc., New York, N.Y. (1967) pp. 28 to 41. That is, little selectivity to particular alkoxylate species is exhibited, especially at higher alkoxylation ratios. For example, FIG. 6 of U.S. Pat. No. 4,223,164 depicts the distribution of alkoxylate species prepared by ethoxylating a fatty alcohol mixture with 60 weight percent ethylene oxide using a potassium catalyst.

The distribution that will be obtained in alkoxylation processes can vary even using the same type of catalyst depending upon the type of organic compound being alkoxylated. For example, with nonylphenol, a Poisson type distribution can be obtained using a potassium hydroxide catalyst. However, with aliphatic alcohols such as decanol, dodecanol, and the like, the distribution is even broader. These distributions are referred to herein as "Conventional Broad Distributions".

Acidic catalysts can also be used, and they tend to produce a narrower, and thus more desirable, molecular weight distributions; however, they also contribute to the formation of undesired by-products and, thus, are not in wide use commercially.

Particular emphasis has been placed on controlling molecular weight distribution of alkoxylation products. One approach has been to strip undesirable alkoxylate species from the product mixture. For instance, U.S. Pat. No. 3,682,849 discloses processes for the vapor phase removal of unreacted alcohol and lower boiling ethoxylate components. The compositions are said to contain less than about 1% of each of non ethoxylated alcohols and monoethoxylates, less than 2% by weight of diethoxylates and less than 3% by weight of triethoxylates. This process results in a loss of raw materials since the lower ethoxylates are removed from the composition. Also, the stripped product still has a wide distribution of ethoxylate species, i.e., the higher molecular weight products are still present in the composition to a significant extent. To circumvent viscosity problems which would normally exist with straight-chain alcohols, about 20 to 30 percent of the starting alcohol is to be branched according to the patent.

Obtaining a narrower distribution of alkoxylated species at lower epoxide reactant to organic compound mole ratios can be readily accomplished. U.S. Pat. No. 4,098,818 discloses a process in which the mole ratio of catalyst (e.g., alkali metal and alkali metal hydride) to fatty alcohol is about 1:1. Ethoxylate distributions are disclosed for Parts C and D of Example 1 and are summarized as follows:

|  | Part C | Part D |
|---|---|---|
| Primary fatty alcohol | 12 carbons | 12 to 14 carbons |
| Moles of ethylene oxide per mole of alcohol | 3.5 | 3 |
| Product molecular weight | 352 | 311 |
| Average ethoxylation | 3.8 | 2.54 |
| Distribution, % | | |
| $E_0$ | 0.7 | 3.8 |
| $E_1$ | 6.3 | 15.3 |
| $E_2$ | 17.3 | 25.9 |
| $E_3$ | 22.4 | 23.8 |
| $E_4$ | 21.2 | 15.9 |
| $E_5$ | 15.6 | 10.7 |
| $E_6$ | 8.6 | 3.5 |
| $E_7$ | 5.6 | 1.2 |
| $E_8$ | 2.3 | — |

The high catalyst content in combination with the low alkylene oxide to alcohol ratio appears to enable a narrow, low ethoxylate fraction to be produced. However, as the ratio of alkylene oxide to alcohol increases, the characteristic, Conventional Broad Distribution of alkali metal catalysts can be expected. Moreover, even though the disclosed process is reported to provide a narrower distribution of ethoxylate species, the distribution is skewed so that significant amounts of the higher ethoxylates are present. For example, in Part C, over 15 percent of the ethoxylate compositions had at least three more oxyethylene groups than the average based on the reactants, and that amount in Part D is over 16 percent.

European Patent Application No. A0095562, published Dec. 12, 1983, exemplifies the ability to obtain high selectivity to low ethoxylate species when low ratios of ethylene oxide reactant to alcohol are employed as well as the tendency to rapidly loose that selectivity when higher ethoxylated products are sought. For instance, Example 1, (described as a 1 mole EO adduct), which reports the use of a diethylaluminum fluoride catalyst, employs 300 grams of a 12 to 14 carbon alcohol and 64 grams of ethylene oxide and Example 5, (described as a 1.5 mole EO adduct) using the same catalyst, employs a weight ratio of alcohol to ethylene oxide at 300:118. Based on the graphically presented data, the distributions appear to be as follows:

|  | Example 1 | Example 5 |
|---|---|---|
| $E_0$ | 27 | 10 |
| $E_1$ | 50 | 36 |
| $E_2$ | 17 | 33 |
| $E_3$ | 4 | 16 |
| $E_4$ | — | 6 |
| $E_5$ | — | 2 |
| $E_6$ | — | 1 |

Even with a small increase in ethoxylation from the described 1 mole EO adduct to the described 1.5 mole adduct, the distribution of ethoxylate species broadened considerably with more of the higher ethoxylates being produced as can be expected from a Conventional Broad Distribution. It may be that the catalyst is consumed in the reaction process so that it is not available to provide the narrower distributions of alkoxylation product mixtures at the high adduct levels.

Several catalysts have been identified that are reported to provide molecular weight distributions for higher ethoxylates that are narrower than those expected from a Conventional Broad Distribution. In particular, this work has emphasized ethoxylation catalysis by derivatives of the Group IIA alkaline earth metals. Interest in these catalysts, which to date has been confined almost exclusively to the production of non-ionic surfactants, stems from their demonstrated capability for providing hydrophobe ethoxylates having narrower molecular weight distributions, lower unreacted alcohol contents, and lower pour points than counterparts manufactured with conventional alkali metal-derived catalysts.

Recently, Yang and coworkers were granted a series of U.S. patents which describe primarily the use of unmodified or phenolic-modified oxides and hydroxides of barium and strontium as ethoxylation catalysts for producing non-ionic surfactants exhibiting lower pour points, narrower molecular weight distributions, lower unreacted alcohol contents and better detergency than counterpart products prepared by state-of-the-art catalysis with alkali metal hydroxides. See U.S. Pat. Nos. 4,210,764; 4,223,164; 4,239,917; 4,254,287; 4,302,613 and 4,306,093. Significantly, these patents contain statements to the effect that the oxides and/or hydroxides of magnesium and calcium do not exhibit catalytic activity for ethoxylation, although they may function in the role of promoters for the barium and strontium compounds (U.S. Pat. No. 4,302,613).

The molecular weight distributions of the ethoxylates disclosed in these patents, while being narrower than conventional distributions, appear not to meet fully the desired narrowness. For example, FIG. 6 of U.S. Pat. No. 4,223,146 depicts the product distribution of an ethoxylate of a 12 to 14 carbon alcohol and 60 percent ethylene oxide using various catalysts. A barium hydroxide catalyst is described as providing a product mixture containing, as the most prevalent component, about 16 percent of the six mole ethoxylate. The distribution is, however, still relatively wide in that the ethoxylate species having three or more oxyethylene groups than the most prevalent component is above about 19 weight percent of the mixture and the distribution is skewed toward higher ethoxylates. The strontium hydroxide catalyst run which is also depicted on that figure appears to have a more symmetrical distribution but the most prevalent component, the seven mole ethoxylate, is present in an amount of about 14.5 weight percent and about 21 weight percent of the composition had three or more oxyethylene groups than the most prevalent component.

Also, U.S. Pat. No. 4,239,917 discloses ethoxylate distributions using barium hydroxide catalyst and a fatty alcohol. FIG. 7 of that patent illustrates the distribution at the 40 percent ethoxylation level with the four mole ethoxylate being the most prevalent component. Over about 19 weight percent of the mixture has three or more oxyethylene groups than the most prevalent component. FIG. 4 depicts the distribution of ethoxylation at the 65 percent ethoxylation level. The nine and ten mole ethoxylates are the most prevalent and each represent about 13 weight percent of the composition. The distribution is relatively symmetrical but about 17 weight percent of the composition has at least three more oxyethylene groups than the average peak (9.5 oxyethylene groups). Interestingly, comparative examples using sodium hydroxide catalyst are depicted on each of these figures and evidence the peaking that can be achieved with conventional base catalysts at low ethoxylation levels, but not at higher ethoxylation levels.

McCain and co-workers have published a series of European patent applications describing the catalytic use of basic salts of alkaline earth metals especially calcium, which are soluble in the reaction medium. These applications further disclose catalyst preparation procedures involving alcohol exchange in respect to the alkoxy moiety of the metal alkoxide catalytic species. See European patent publication Nos. 0026544, 0026547, and 0026546, all herein incorporated by reference. See also U.S. Ser. No. 454,560, filed Dec. 30, 1982 (barium-containing catalyst) and now abandoned. These workers have also disclosed the use of strong acids to partially neutralize and thereby promote the catalytic action of certain alkaline earth metal derivatives. See U.S. Ser. No. 370,204, filed Apr. 21, 1982 and now U.S. Pat. No. 4,453,022, and Ser. No. 454,573 filed Dec. 30, 1982 (barium-containing catalyst) and now U.S. Pat. No. 4,453,023, both herein incorporated by reference. These workers also tend to confirm Yang's findings as to calcium oxide, in that McCain et al. teach that calcium oxide does not form a lower alkoxide when treated with ethanol.

In particular, calcium metal or calcium hydride is typically the starting material used by McCain et al. to make the calcium-containing catalyst. These starting materials, however, are expensive. Consequently, a desire exists to use commonly found sources of calcium, such as calcium oxide (quicklime) and calcium hydroxide (slaked lime), to make calcium-containing catalysts for alkoxylation. Moreover, quicklime and slaked lime are by far the cheapest, most plentiful, least noxious, and most environmentally-acceptable of all the alkaline earth metal derivatives.

The calcium-containing catalysts disclosed by McCain et al. provide enhanced selectivities to higher alkoxylate species as compared to mixtures produced using conventional potassium hydroxide catalyst. Indeed, bases exist to believe that these calcium-containing catalysts provide narrower distributions of alkoxylates than those provided by strontium- or barium-containing catalysts. However, there is still need for improvement in providing a narrower yet distribution of alkoxylation products, particularly a distribution in which at least one component constitutes at least 20 weight percent of the composition and alkoxylation products having more than three alkoxyl groups than the average peak alkoxylation component comprise very little of the product mixture.

Copending U.S. patent application Ser. No. 621,991, filed June 22, 1984 and now abandoned, herein incorporated by reference, relates to processes for preparing alkoxylation mixtures having relatively narrow alkoxylation product distributions using modified, calcium-containing catalysts. Processes are also disclosed for making alkoxylation catalysts using calcium oxide and-/or calcium hydroxide as sources for the catalytically-active calcium. The alkoxylation product mixtures disclosed therein have a narrow and balanced distribution of alkoxylation species. The disclosed product mixtures are relatively free from large amounts of substantially higher alkoxylation moieties, i.e., those having at least three more alkoxyl groups than the average peak alkoxylate specie. It is stated therein that narrow distributions can be obtained where the most prevalent alkoxylation moiety has four or greater alkoxy units, that is, in the regions in which conventional catalysts provide a relatively wide range of alkoxylation species.

DISCLOSURE OF THE INVENTION

This invention relates to novel heterogeneous (organic polymer-supported) alkoxylation catalysts and to processes for making the heterogeneous (organic polymer-supported) alkoxylation catalysts using calcium oxide and/or calcium hydroxide as sources for the catalytically-active calcium. This invention further relates to novel alkoxylation product mixtures having relatively narrow alkoxylation product distributions and negligible amounts of catalyst residues and also to processes for preparing the alkoxylation product mixtures using heterogeneous (organic polymer-supported), modified calcium-containing catalysts.

The heterogenous alkoxylation catalysts of this invention are supported on a crosslinked organic polymer substrate and characterized by the structural feature that the calcium atom is chemically bonded to a crosslinked, microporous, macroporous or physically expanded polymeric support through a carbocyclic or heterocyclic linkage as illustrated by the following formula:

$$R_1-R_2-X_1-Ca-X_2-R_3 \qquad (i)$$

wherein:

$R_1$ is an organic polymeric residue which has a crosslinked, microporous, macroporous or physically expanded structure;

$R_2$ is a carbocyclic or heterocyclic residue;

$X_1$ and $X_2$ are independently oxygen or sulfur; and $R_3$ is hydrogen or an organic residue of an organic compound having at least one active hydrogen.

In a preferred aspect of this invention, the heterogeneous alkoxylation catalysts of formula (i), including the alcohol-exchanged derivatives thereof as described hereinafter, are modified by partial neutralization with an inorganic oxyacid having a multivalent anion such as sulfuric acid, phosphoric acid, carbonic acid, pyrosulfuric acid and the like, or by metal salts of the inorganic oxyacids such as aluminum sulfate, zinc sulfate, zinc phosphate and the like. The inorganic oxyacids and the metal salts thereof are at times referred to hereinafter as "modifiers". These partially neutralized catalysts are believed to have complex structures which are probably comprised of a mixture of species, certain of which may not even be catalytically active. Those species which are catalytically active are believed to have structures of the type depicted by the following formula:

$$[R_1-R_2-X_1-Ca_f][Y_1[Ca-X_2-R_3]_g \quad \text{(ii)}$$

wherein $R_1$, $R_2$, $R_3$, $X_1$ and $X_2$ are as defined hereinabove, $Y_1$ is a multivalent oxyacid anion of valence 2 to 4 and f and g are integers having a value such that the sum f+g is equal to the valence of $Y_1$. It is understood that formula (ii) is speculation only.

Another aspect of the invention provides a method for preparing a heterogeneous (organic polymer-supported) alkoxylation catalyst, which method comprises (i) preparing a catalyst precursor by reacting an organic polymer which has a crosslinked, microporous, macroporous or physically expanded structure with a carbocyclic or heterocyclic compound, (ii) solubilizing, at least in part, calcium oxide and/or calcium hydroxide, or mixtures thereof, by mixing any of them with an activator to form a calcium containing composition having titratable alkalinity, and (iii) reacting the catalyst precursor with the calcium-containing composition under effective reaction conditions to produce the alkoxylation catalyst. The term "solubilizing" as used herein is intended to mean that the calcium is provided in an active form which is not the case when calcium is in the form of calcium oxide or calcium hydroxide, hence a solubilization is believed to exist; however, the term is not intended to be limiting to the formation of a truly dissolved calcium specie (which may or may not exist).

The solubilization is effected by mixing any of calcium oxide and calcium hydroxide with an activator having the general formula $Z_a-X-Q-Y-Z'_b$ wherein X and Y are the same or different electronegative (relative to carbon), hetero (i.e., non-carbon) atoms selected from the group consisting of oxygen, nitrogen, sulfur and phosphorous; a and b are the same or different integers satisfying the valency requirements of X and Y; Q is any organic radical which is electropositive or essentially neutral relative to X and/or Y, which does not prevent the solubilization, and which contains at least one carbon atom and preferably has the formula

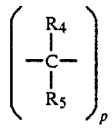

wherein $R_4$ and $R_5$ are the same or different and are selected from the group consisting of hydrogen and lower alkyl or alkylene groups of one to four carbon atoms, and p is an integer from 1 to 6, preferably 2 to 4; Z and Z' are the same or different and are either hydrogen or an organic radical which does not interfere with the function of the activator for its intended purpose, i.e., its solubilizing function, thereby forming a calcium-containing composition which is then reacted with the catalyst precursor to produce an essentially solid catalyst which is catalytically active in the alkoxylation of compounds having active hydrogens, especially alcohols.

Solubilization of calcium oxide or calcium hydroxide results in the production of an alkaline slurry, which alkalinity can be detected and measured by titration and which is referred to herein as "titratable alkalinity".

The heterogeneous catalyst composition can be directly contacted with alkylene oxides to form alkoxylates of the activator itself, if having an active hydrogen, to produce alkoxylates. If the activator does not have an active hydrogen, excess activator should preferably be removed prior to alkoxylation.

According to further embodiments of this aspect of the invention, an exchange reaction is carried out after the reaction of the calcium-containing composition with the catalyst precursor under conditions at which an exchange reaction will occur, with at least one organic compound having an active hydrogen, e.g., an alcohol, having a higher boiling point (and usually a longer carbon chain length) than said activator to form the corresponding, catalytically active higher boiling derivative of calcium. This latter catalytic species can then be directly contacted with alkylene oxide to form alkoxylates of the higher boiling material.

The alkoxylation processes of this invention involve the condensation reaction of an alkylene oxide and at least one organic compound having at least one active hydrogen in the presence of a catalytically effective amount of a heterogeneous (organic polymer-supported), modified calcium-containing catalyst as described above. The heterogeneous modified catalyst comprises a strong, inorganic oxyacid provided in an amount of about 0.2 to 0.9, e.g., 0.35 to 0.85, often, about 0.45 to 0.75, times that required to neutralize the catalyst composition, which is sufficient to narrow the distribution of the alkoxylation product mixture and provide at least one alkoxylation specie in an amount of at least about 20 weight percent of the mixture. In addition, alkoxylation products are provided which are essentially neutral in pH and free from catalyst residues. The heterogeneous modified catalyst is prepared under sufficient agitation to ensure a relatively uniform product. The preferred oxyacid is sulfuric acid. Frequently, the heterogeneous modified catalyst is prepared in a medium having a dielectric constant at 25° C. or its normal boiling point, whichever is less, of at least about 10, preferably, at least about 20, say, about 20 to 50, and frequently about 25 or 30 to 45.

By this invention, alkoxylation product mixtures are provided which have a narrow, but balanced distribution of alkoxylation species. These product mixtures are relatively free from large amounts of substantially higher alkoxylation moieties, i.e. those having at least three more alkoxyl groups than the average peak alkoxylate specie. Advantageously, these narrow distributions can be obtained where the most prevalent alkoxylation moiety has four or greater alkoxy units, that is, in the regions in which conventional catalysts provide a relatively wide range of alkoxylation species. The product mixtures are essentially neutral in pH and contain negligible amounts of catalyst residues, thereby requiring no post-treatment.

The alkoxylation product mixtures prepared by the processes of this invention are characterized as the condensation reaction products of alkylene oxides and organic compounds having at least one active hydrogen in which the mole ratio of reacted alkylene oxide per active hydrogen is at least about 4, say, about 4 to 16 or 24, preferably about 5 to 12. The product mixtures have at least one alkoxylation moiety which constitutes at least about 20, say, about 20 to 30 or 40, and most often about 20 to 30, weight percent of the composition. The alkoxylation mixtures of this invention also have a relatively symmetrical distribution. Hence, the portion of the product mixture having three or more oxyalkylene unit groups (per active hydrogen site of the organic compound) than the peak alkoxylation specie is relatively minor, e.g., often less that about 12, say, less than 10, and often about 1 to 10, weight percent of the mixture. Similarly, the alkoxylation species having fewer oxyalkylene groups (per active hydrogen site of the organic compound) by three or more oxyalkylene groups from the average peak alkoxylation specie is usually relatively minor, e.g., less than about 15, say, less than about 10, often about 0.5 to 10, weight percent of the composition. Generally, the one oxyalkylene unit higher and the one oxyalkylene unit lower alkoxylates in respect to the most prevalent alkoxylation specie are present in a weight ratio to the most prevalent alkoxylation specie of about 0.6:1 to 1:1.

The preferred alkoxylation product mixtures of this invention correspond to the formula $$P_n = A \times e^{-(n-\bar{n})/2.6 + 0.4n}.$$

wherein n is the number of oxyalkylene groups per reactive hydrogen site for an alkoxylation specie (n must equal at least one) of the composition, $\bar{n}$ is the weight average oxyalkylene number, A is the weight percent of the most prevalent alkoxylation specie in the mixture and $P_n$ is, within plus or minus two percentage points, the weight percent of the alkoxylation specie having n oxyalkylene groups (per active hydrogen site) in the mixture. This distribution relationship generally applies where n is between the amount of $\bar{n}$ minus 4 to the amount of $\bar{n}$ plus 4.

For purposes herein, the average peak alkoxylation specie is defined as the number of oxyalkylene groups (per active hydrogen site) of the most prevalent alkoxylation specie when the next higher and lower homologs are each present in a weight ratio to the most prevalent alkoxylation specie of less than 0.9:1. When one of the adjacent homologs is present in a weight ratio greater than that amount, the average peak alkoxylation specie has an amount of oxyalkylene groups equal to the number average of those of the two species. The weight average oxyalkylene number is the weight average of the oxyalkylene groups of the alkoxylation species in the mixture (including unreacted alcohol), i.e., $\bar{n}$ equals the sum of $(n)(P_n)$ for all the species present divided by 100.

Preferred alkoxylation product mixtures of this invention include poly(oxyethylene)glycols, i.e., CARBOWAX®, and fatty alcohol ethoxylates, i.e., TERGITOL®. CARBOWAX® is the registered trademark of Union Carbide Corporation for a series of poly(oxyethylene)glycols. Ethylene glycol can be used to make the CARBOWAX® poly(oxyethylene)glycols or the CARBOWAX® poly(oxyethylene)glycols can be used to make higher molecular weight CARBOWAX® poly(oxyethylene)glycols. For example, CARBOWAX® poly(oxyethylene)glycol 200 can be used to make CARBOWAX® poly(oxyethylene)-glycol 400. Specifically, the CARBOWAX® poly(oxyethylene)glycols are liquid and solid polymers of the general formula $H(OCH_2CH_2)_wOH$, where w is greater than or equal to 4. In general, each CARBOWAX® poly(oxyethylene)glycol is followed by a number which corresponds to its average molecular weight.

Generally, the invention process is not preferred for using CARBOWAX® poly(oxyethylene)glycols having an average molecular weight above about 600 to 800 as starting materials because such CARBOWAX® poly(oxyethylene)glycols are solids at room temperature (although they are liquid at the reaction temperatures, e.g., 110° C.). Examples of useful CARBOWAX® poly(oxyethylene)glycols are: CARBOWAX® poly(oxyethylene)glycol 200, which has an average w value of 4 and a molecular weight range of 1 90 to 210; CARBOWAX® poly(oxyethylene)glycol 400, which has an average w value between 8.2 and 9.1 and a molecular weight range of 380 to 420; and CARBOWAX® poly(oxyethylene)glycol 600, which has an average w value between 12.5 and 13.9 and a molecular weight range of 570 to 630.

TERGITOL® is the registered trademark of Union Carbide Corporation for a series of ethoxylated nonylphenols, primary and secondary alcohols, i.e., nonionic surfactants, and the sodium salts of the acid sulfate of secondary alcohols of 10 to 20 carbon atoms, i.e., anionic surfactants. Examples of the TERGITOL® nonionic surfactants include TERGITOL® S Nonionics which have the general formula $CH_3(CH_2)_xCH(CH_3)—O—(CH_2CH_2O)_yH$ wherein x is a value of 9-11 and y is a value of about greater than 1. Examples of the TERGITOL® anionic surfactants include TERGITOL® Anionic 08, which is $C_4H_9CH(C_2H_5)CH_2SO_4$—Na; TERGITOL® Anionic 4, which is $C_2H_9CH(C_2H_5)C_2H_4CH$—$(SO_4$-Na$)CH_2CH(CH_3)_2$; and TERGITOL® Anionic 7, which is $C_4H_9CH(C_2H_5)C_2H_4CH$—$(SO_4$-Na$)C_2H_4CH(C_2H_5)_2$.

DETAILED DESCRIPTION

Figure 1:
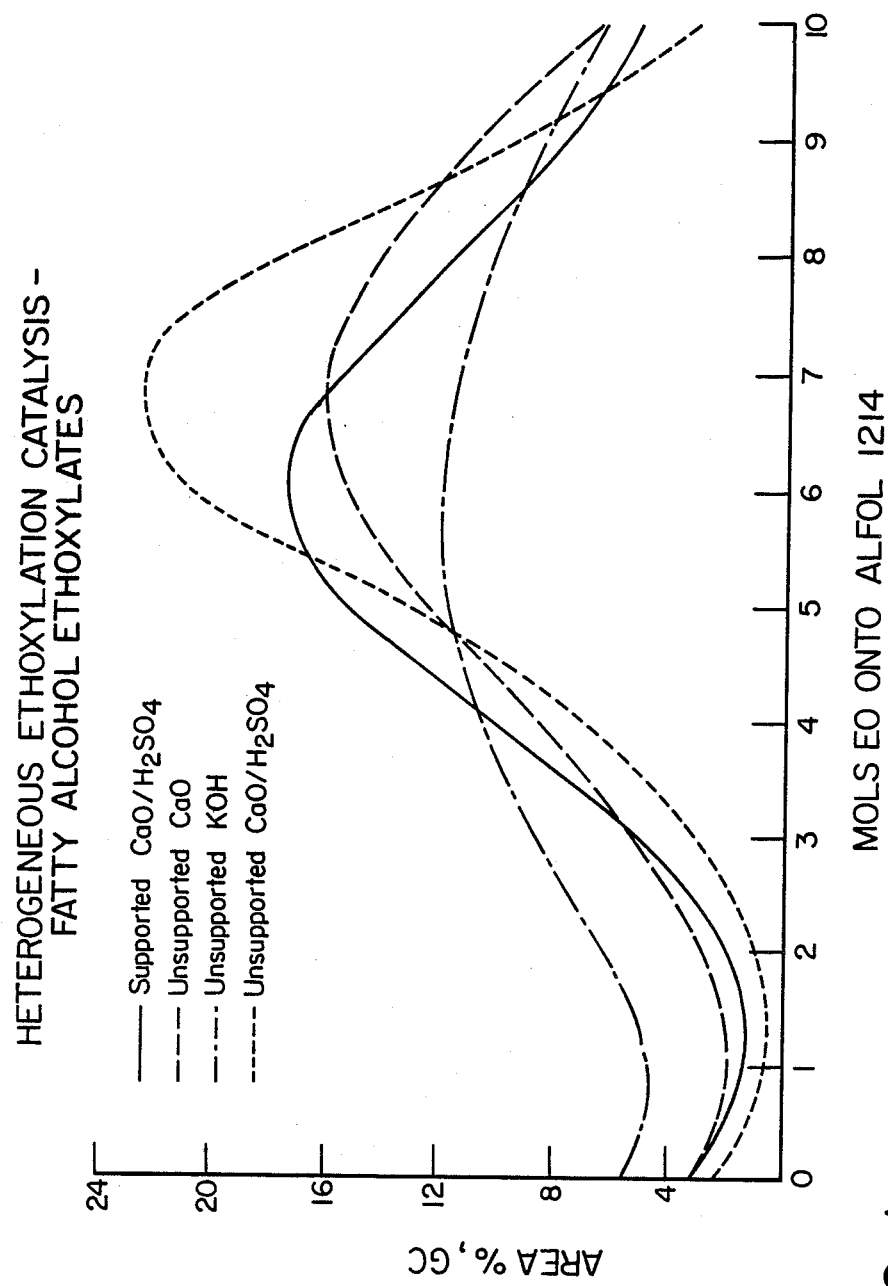
FIG. 1 depicts the average ethoxylate distribution for fatty alcohol ethoxylates prepared in Example 11 hereinafter (supported $CaO/H_2SO_4$) as well as unsupported CaO, unsupported KOH and unsupported $CaO/H_2SO_4$. The average ethoxylate distributions were obtained by averaging (area % values) individual gas chromatography scans.

The organic polymer-supported calcium-containing catalysts of this invention are heterogeneous catalysts, that is, they are useful in heterogeneous catalysis. Heterogeneous catalysis involves a catalytic reaction in which the reactants and the catalyst comprises two separate phases, e.g., gases over solids, or liquids containing finely-divided solids as a disperse phase. By way of contrast, homogeneous catalysis involves a catalytic reaction in which the reactants and the catalyst comprise only one phase, e.g., an acid solution catalyzing other liquid components. The alkoxylation reactions of this invention occur on the surface of the solid catalyst particles. The individual steps of heterogeneous catalytic processes probably involve the following: (1) diffusion of reactants to surface; (2) adsorption of reactants on surface; (3) reaction of adsorbed reactant to form adsorbed product; (4) desorption of product; and (5) diffusion of product into main stream of a liquid or vapor.

As indicated above, the heterogeneous alkoxylation catalysts of this invention are supported on a crosslinked organic polymer substrate and characterized by the structural feature that the calcium atom is chemically bonded to a crosslinked, microporous, macroporous or physically expanded polymeric support through a carbocyclic or heterocyclic linkage as illustrated by the following formula:

$$R_1-R_2-X_1-Ca-X_2-R_3 \quad (i)$$

wherein:

$R_1$ is an organic polymeric residue which has a crosslinked, microporous, macroporous or physically expanded structure;

$R_2$ is a carbocyclic or heterocyclic residue;

$X_1$ and $X_2$ are independently oxygen or sulfur; and $R_3$ is hydrogen or an organic residue of an organic compound having at least one active hydrogen.

In a preferred aspect of this invention, the heterogeneous alkoxylation catalysts of formula (i), including the alcohol-exchanged derivatives thereof, are modified by partial neutralization with an inorganic oxyacid having a multivalent anion such as sulfuric acid, phosphoric acid, carbonic acid, pyrosulfuric acid and the like, or by metal salts of the inorganic oxyacids such as aluminum sulfate, zinc sulfate, zinc phosphate and the like. These partially neutralized catalysts are believed to have complex structures which are probably comprised of a mixture of species, certain of which may not even be catalytically active. Those species which are catalytically active are believed to have structures of the type depicted by the following formula:

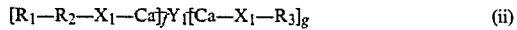

$$[R_1-R_2-X_1-Ca]_fY_1[Ca-X_1-R_3]_g \quad (ii)$$

wherein $R_1$, $R_2$, $R_3$, $X_1$ and $X_2$ are as defined hereinabove, $Y_1$ is a multivalent oxyacid anion of valence 2 to 4 and f and g are integers having a value such that the sum $f+g$ is equal to the valence of $Y_1$. It is understood that formula (ii) is speculation only.

The alkoxylation product mixtures of this invention ar enabled by the use of heterogeneous (organic polymer-supported) calcium-containing catalysts that have been modified by strong, inorganic oxyacids or metal salts thereof sufficient to provide a defined narrow distribution of alkoxylation products. The alkoxylation conditions may otherwise vary while still obtaining a narrower distribution of alkoxylate products.

The modifier of the catalyst is preferably a polyvalent acid and contains at least one, most often at least about 2, oxygen atoms that are conventionally depicted as double bonded to the nucleus atom. Such acids include, for example, sulfuric and phosphoric acid; however, in general the most narrow distributions are obtained using sulfuric acid.

The amount of modifier employed and the manner in which it is introduced to prepare the catalyst can be determinative of whether the desired narrow distribution with at least one alkoxylation specie being present in an amount of at least about 20 weight percent of the composition, is achieved. While not wishing to be limited to theory, it is believed that active catalysts for producing narrow distributions of alkoxylation products comprise a calcium atom in association with the modifier anion in a manner in which the calcium atom is activated as illustrated by formula (ii) hereinabove.

In general, at the time of modification, the calcium-containing catalyst may be represented by formula (i) hereinabove wherein $-X_2R_3$ is an organic-containing residue of an organic compound having an active hydrogen, and $X_2$ is oxygen, nitrogen, sulfur or phosphorous. $R_3$ may thus also contain double bonded oxygen (the organic compound was a carboxylic acid), hetero atom such as oxygen, sulfur, nitrogen and phosphorous (e.g., the organic compound was a glycol, polyamine, ether of a glycol or the like). Frequently, $R_3$ comprises 1 to 20 carbons.

The amount of modifier added is in an amount of about 0.2 to 0.9, say, about 0.45 to 0.75, times that required to neutralize the catalyst composition. Frequently, the molar ratio of modifier sites (sulfuric acid has two acid sites and phosphoric acid has three acid sites) to calcium atoms is about 0.5:1 to 1.8:1.

The modifier appears to enable the desired catalytically active calcium species to form; however, it has been found that depending upon other conditions during the modification, different amounts of modifier will provide the optimum catalyst in terms of selectivity and reaction rate during an alkoxylation process. Accordingly, an aspect of the invention is providing a level of modification sufficient to achieve the narrow distribution of alkoxylate product mixtures.

The medium containing the heterogeneous calcium catalyst can also affect whether the resulting modified calcium catalyst enables the desired narrow distribution of alkoxylation products to be formed. If the medium comprises as the predominant component, i.e., solvent, a material that has a low dielectric constant, the modifier can form a separate liquid phase and increased difficulty in obtaining an intimate admixture may be observed. On the other hand, with solvents that are too polar, the organic moiety in association with the calcium atom may be displaced with the solvent. Accordingly, undue amounts of water are typically avoided during the modification of the calcium-containing catalyst. Most often, the medium and the organic compound providing the moiety on the calcium atom are the same. Particularly convenient media include ethylene glycol, propylene glycol, diethylene glycol, lycerol, butanediols, 1,3 propanediol, and the like. Conveniently, the medium employed, if not intended to be a reactant for producing alkoxylates, should have a sufficiently low boiling point that can readily be removed from the catalyst and organic compound reactant mixture by distillation. Most often, the medium comprises a solvent having at least two hetero-atoms such as the activators described herein.

The modifier is preferably added while the calcium-containing catalyst is being vigorously agitated. In this regard, a slow addition of the modifier to the calcium-containing catalyst is preferred. Generally, less than 10 percent of the modifier to be added is added to the calcium-containing catalyst at any one time. The addition of the modifier can be conducted at a convenient temperature, e.g., about 10° C. to 160° C., say, about 50° C. to 150° C. Preferably, a nitrogen atmosphere is advantageous.

The calcium-containing catalyst having a substituent of the formula $-X_2R_3$ may be prepared in any suitable manner. For example, a catalyst precursor can be prepared by reacting an organic polymer which has a crosslinked, microporous, macroporous or physically expanded structure with a carbocyclic or heterocyclic compound. Then, calcium metal, hydride or acetylide or other suitable source of calcium may be reacted with an organic compound containing an active hydrogen atom of the formula $HX_2R_3$. With compounds having higher molecular weights, e.g., 4 or more carbons, it is generally preferred to use a lower molecular weight and more reactive and volatile compound of the formula $HX_2R_3$ (e.g., of 1 to about 3 carbons, especially compounds such as ethanol, ethylamine, ethylene glycol and the like) and then exchange that substituent with the higher molecular weight substituent while removing the lower molecular weight material by volatilization. Alternatively, the calcium-containing catalyst can be prepared from quicklime or slaked lime by the process disclosed hereinafter. The catalyst precursor is then reacted with the source of the catalytically-active calcium to produce the heterogeneous alkoxylation catalyst.

The compounds having the formula $HX_2R_3$ include those organic compounds having active hydrogens described in connection with the alkoxylation products of this invention, such as alcohols, phenols, carboxylic acids and amines. Most often, the compounds having the formula $HX_2R_3$ are alcohols. When an exchange reaction is to be conducted to provide a higher molecular weight substituent on the calcium atom, it is generally preferred to conduct the acid modification prior to exchange and use a lower molecular weight material for the replacement substituent to enhance the acid modification process.

The preparation of the modified calcium catalyst composition from calcium metal, hydride or acetylide or other suitable source of calcium is typically conducted at elevated temperatures, e.g., from about 30° C. to 200° C. or more, and in a liquid medium. The organic compound which provides the substitution is normally provided in excess of that required for reaction with the calcium reactant. Hence, the weight ratio of calcium to the organic compound frequently is within the range of about 0.01:100 to 25:100. The reaction may, if desired, be conducted in the presence of an inert liquid solvent. The exchange reaction is also conducted under elevated temperature and, optionally, under reduced pressure to facilitate removal of the more volatile components. Temperatures may range from about 50° C. to 250° C., say, about 80° C. to 200° C. or 250° C., and pressures (absolute) are often in the range of 1 millibar to 5 bars, e.g., about 10 millibars to 2 bars.

It is usually desired that the organic substituent on the modified, calcium-containing catalyst composition correspond to the "starter" component for the alkoxylation process. The starter component is the organic compound having at least one active hydrogen with which the alkylene oxide reacts.

The alkoxylation is conducted using a catalytically-effective amount of the calcium-containing catalyst, e.g., about 0.01 to 10, often about 0.5 to 5, weight percent based on the weight of the starter component. The catalysts substantially retain their activities during the alkoxylation, regardless of the amount of alkylene oxide employed. Thus, the amount of catalyst can be based on the amount of starter provided to the alkoxylation zone and not the degree of alkoxylation to be effected. Moreover, the catalyst can be recovered (since it is a solid) from the reaction product and reused. Indeed, it has been found that conditioned (preused) catalysts may provide superior products. The catalysts also appear to be relatively storage stable and are relatively tolerant of water. Hence, storage can be effected under convenient conditions.

Normally, the catalyst and the starter component are admixed and then the alkylene oxide is added at the reaction temperature until the desired amount of alkylene oxide has been added, then the product is neutralized and can be finished, if desired, in any procedure including stripping unreacted starter material from the product mixture, filtration, or further reaction, e.g., to form sulfate.

The temperature of the alkoxylation is sufficient to provide a suitable rate of reaction and without degradation of the reactants or reaction products. Often, the temperatures range from between about 50° C. and 270° C., e.g. from about 100° C. to 200° C. The pressure may also vary widely, but when low boiling alkylene oxides such as ethylene oxide..and propylene oxide are employed, a pressurized reactor is preferably used.

The alkoxylation reaction medium is preferably agitated to ensure a good dispersal of the reactants and catalyst throughout the reaction medium. Also, the alkylene oxide is usually added at a rate approximating that which it can be reacted.

While typically alkoxylation products are neutralized, upon removal of the catalysts employed in accordance with the processes of the invention, the alkoxylation product mixture is relatively neutral, e.g., about a pH of 6, regardless of the pH of the catalyst containing product. Neutralization, however, may assist in the recovery of the catalyst from the alkoxylation product mixture. When neutralizing, acids that may tend to form catalyst-containing gel structures or solids that clog filtering apparatus should be avoided. Conveniently, sulfuric acid, phosphoric acid, propionic acid, benzoic acid and the like are used.

The present invention provides a procedure whereby calcium oxide (quicklime) and its hydrated form, calcium hydroxide (slaked lime) (both herein referred to as "lime"), can be effectively used to prepare catalytic species which are active in the alkoxylation of organic compounds having at least one active hydrogen such as alcohols, especially long-chain fatty alcohols, carboxylic acids, amines, polyols and phenols. This is accomplished by the following general procedure.

A catalyst precursor is prepared by reacting an organic polymer which has a crosslinked, microporous, macroporous or physically expanded structure with a carbocyclic or heterocyclic compound. To be of utility as a support for the heterogeneous catalysts of this invention, the organic polymer should (i) possess a network (crosslinked) structure of an insoluble, yet solvent-swellable type, (ii) possess microporous, macroporous or physically expanded morphology conferring high surface area, low density and liquid permeability, (iii) possess satisfactory chemical, physical and mechanical stability, and (iv) possess functionality of an aromatic type or of a precursor type through which aromatic functionality can be introduced by chemical modification.

A large number and variety of organic polymers can have utility in the preparation of the polymer-supported calcium catalysts of this invention. Such organic polymers are conventional materials known in the art. Two preferred general classes of polymers include the (1) polystyrenics, made by free radical polymerization, and the (2) phenolics, made by condensation polymerization.

A versatile class of organic polymeric supports is the polystyrene polymers; these polymers, in their simplest form, are copolymers of styrene with divinyl benzene wherein the desired degree of crosslinking is readily controlled by the quantity of divinyl benzene used. The copolymers are produced by suspension polymerization techniques which permit the products to be formed as spherical beads of controllable size (over a range from about 20-400 mesh) and morphology (microreticular or microreticular). Functionalized versions of such resins can be made either directly by using the appropriately functionalized styrene monomer or indirectly by performing appropriate chemical reactions on copolymers made from styrene itself.

From the standpoint of supported catalyst synthesis efforts, a preferred class of styrene/divinyl benzene copolymers is that known as Merrifield ® Resins, developed by R. Merrifield for use in the polymer-supported synthesis of peptides. The Merrifield ® Resins are chloromethylated styrene/divinyl benzene resins wherein the degree of functionalization can be readily controlled. The chloromethyl function is highly reactive with a broad spectrum of reagents, so that resins having virtually any desired type of functionality can be obtained from these intermediates through well-characterized chemical transformations. These Merrifield ® Resins are preferred materials for preparing the catalyst precursors to the supported calcium catalysts of the instant invention. Thus, preferred catalyst precursors can be prepared either by alkylating the desired carbocyclic or heterocyclic compound, e.g., phenol or thiophenol, with a Merrifield ® Resin under Friedel-Crafts conditions or by condensing a monoalkali metal salt of the carbocyclic or heterocyclic compound, e.g., diphenol or dithiophenol, with Merrifield ® Resin under Williamson etherification conditions. Many synthetic routes to such aryloxy- or arylthio-containing resins from the chloromethylated resin materials are known in the art.

Another class of polymers which is particularly useful for making the supported calcium catalysts of this invention is the phenolic resins. These polymers are prepared by condensing phenol or a substituted phenol with some aldehyde, usually formaldehyde, in the presence of caustic under conditions such that the formaldehyde reactant is in excess. This condition promotes crosslinking, a necessary property of a polymeric support. The degree of crosslinking can be controlled by the charge ratio of the reactants and a spherical, hollow bead form of the resin known as microballons can be produced by expanding the curing polymeric mass with a gas such as nitrogen released thermally from a chemical blowing agent in the formulation. These hollow spheres have an extremely low bulk density and a porous structure which is permeable to, and swollen by, many organic liquids. The spheres are typically of size from about 0.005 to 0.15 mm, or about 150 mesh on average. As precursors to the supported calcium catalysts, these phenolic "microballons" are attractive because (1) they are suitable for calcium loading as received, i.e., the aryloxy or arylthio functionality is already present, (2) they accept high levels of calcium loading, (3) they can be fine-tuned for ultimate catalytic activity by using appropriately substituted phenols in the original condensation, (4) they have good chemical stability, and (5) they are an article of commerce.

There are a large number of conventional synthetic techniques and classical reactions which can be employed to prepare the catalyst precursors. In the case of the crosslinked polystyrene resins, for example, the three principal alternative methods for introducing the required aryloxy or arylthio functionality are:

1. Direct route, wherein the required functionality is performed on the monomer itself and this desirably-functionalized monomer is then copolymerized with divinylbenzene;

2. Indirect route, wherein the desired functionality is introduced via a "grafting" approach, such as, for example, the Friedel-Crafts reaction of a phenol or thiol with a reactive functionalized resin such as the chloromethylated resins (Merrifield ® Resins); and 3. A semi-direct approach, wherein the monomer itself is functionalized as in the direct route above, but this functionality is of a precursor type requiring post-modification to convert it into the required aryloxy or arylthio functions. Examples of this approach include the use of a methoxystyrene monomer and acid cleavage of the —$OCH_3$ group in the polymer to an —OH group or the use of a nitrostyrene monomer followed by reduction, diazotization and hydrolysis of the polymer to convert the original —$NO_2$ groups into —OH groups.

In the case of phenolic resin type supports, post-modification of the resin is normally not an issue because the required aryloxy or arylthio functionality is introduced directly via one of the monomers used in the condensation polymerization. With such supports, however, chemical post-modifications can be employed, if so desired, to modify either the acidity of the —OH or —SH function or its steric environment. It is also possible, of course, to use mixtures of phenols or thiophenols in these condensations.

A preferred type of catalyst precursor which can be utilized is one made by reaction of a crosslinked functionalized polystyrene resin (e.g., the chloromethylated Merrifield ® Resins) with a crosslinked, expanded phenolic resin to make a catalyst precursor which is comprised of a polymeric support type resin graft-modified with a polymeric resin containing the required aryloxy or arylthio functionality. All such precursor compositions are intended to be included within the scope of this invention without limitations with regard to method of preparation.

The carbocyclic or heterocyclic compound used herein is an important aspect of this invention. A commercially useful heterogeneous catalyst must exhibit not only an acceptable level of catalytic activity, but also outstanding chemical and physical stability. These are the minimum qualifications which the catalyst must possess; not surprisingly, the second characteristic is frequently more difficult to achieve than the first. This is certainly the case in the instant invention. Indeed, an important aspect of this invention is its definition of a structural feature important to the preparation of a chemically stable, supported calcium catalyst; that is, a catalyst which does not release calcium ions into the reaction medium and, consequently, provides an ethoxylated product which is essentially neutral in pH and free from catalyst residues.

The structural feature which is responsible for imparting this chemical stability to the catalysts herein described is the carbocyclic or heterocyclic residue, e.g., the phenoxy or thiophenoxy functionality, which serves to bind the metal atom (calcium) to the organic polymeric support. In the generic formulae (i) and (ii) above this chemical linkage appears as the —$R_2$—$X_1$—Ca— grouping wherein $X_1$ may be either oxygen (a phenoxide) or sulfur (a thiophenoxide). The stability of the —$X_1$Ca— chemical bond is related to the acidity of the parent phenols and/or thiophenols. As a chemical class, phenols and thiophenols are relatively weak acids with dissociation constants typically in the order of $10^{-9}$ to $10^{-11}$ (pKas of about 9–11). On an acidity scale, the phenols/thiophenols lie about midway between organic (carboxylic) acids with pKas of about 4 to 6 and aliphatic alcohols with pKas of about 14–16. Since the undesirable reaction of calcium release from the supported catalyst involves attack of some acidic species at the metal atom site on the catalyst with concomitant release of the conjugate acid of $R_2X_1$, (i.e., $R_2X_1H$), the —$X_1$—Ca— bond should be stable toward any acidic species whose dissociation constant is substantially below that of the $R_2X_1H$ species which would be liberated in the calcium release process. Accordingly, the $X_1$—Ca bond in the —$R_2$—$X_1$—Ca— function should be stable in the aliphatic alcohol environment prevailing in typical alkoxylation processes and calcium release from the supported catalyst should not occur. The —Ca—$X_2$— bond of —Ca—$X_2$—$R_3$ group, by way of contrast, is unstable toward aliphatic alcohols because the conjugate acid ($HX_2R_3$) of —$X_2R_3$ which is displaced is comparable in pKa to the alcohol(s) comprising the alkoxylation medium. Thus, the process of alkoxide exchange occurs freely around the —Ca—$X_2$— group and normally will continue until the requisite quantity of alkylene oxide monomer has been consumed in production of the desired alkoxylate product.

The important role of the carbocyclic or heterocyclic residue, e.g., the aryloxy/arylthio functionality, in the performance of the supported calcium catalysts is apparent from the foregoing discussion. An important aspect of this invention lies in the definition of this particular functionality as important to the successful implementation of the supported calcium alkoxylation catalyst. Whereas the presence of aryloxy or arylthio functionality is important in the catalysts of this invention, there are but few limitations on the types of aryloxy or arylthio species which are suitable for use. The primary limitation imposed upon the aryloxy or arylthio functional group is that its conjugate acid, i.e., the parent phenol or thiophenol, have a dissociation constant falling within the range of $10^{-7}$ to $-10^{13}$, or a pKa in the range of 7 to 13. Providing this limitation is met, the aryloxy or arylthio function can be of the monocyclic type, e.g., phenol itself, polycyclic type, e.g., tetralin, indene, flourene, anthracene, etc., or heterocyclic type, e.g., benzofuran, benzopyran, etc. Further, the aryloxy or arylthio function may be substituted with any other functional groups in any number, providing that such substitution neither causes the dissociation constant of the conjugate acid of the aryloxy or arylthio species to fall outside the $10^{-7}$ to $10^{-13}$ range nor interferes chemically with either the progress of the calcium-loading reaction or the performance of the finished supported calcium alkoxylation catalyst. The aryloxy or arylthio species may also be of polymeric type, e.g., $R_2$—OH or $R_2$—SH terminated linear polymers such as that derived from the condensation of hydroquinone with 1,2-dibromoethane or that from condensation of 4,4'-biphenol with bis(4-chlorophenyl)sulfone.

Polymeric aryloxy or arylthio species in fact are frequently preferred types because, upon reaction with an appropriately functionalized polymeric support and subsequent calcium loading, they afford supported catalysts having the catalytically active (calcium atoms) sites far removed from the support itself and, hence, free from steric hinderance effects which might reduce catalytic activity.

Lime is then contacted with an activator under conditions at which the lime and the activator will react or interact to form one or more catalytically active derivatives, hereinafter referred to collectively as "the derivative". The activator may be any compound having the formula $$Z_a-X-Q-Y-Z'_b$$

wherein the various terms are as previously defined. Heterogeneous alkoxylation catalysts incorporating the derivatives of this reaction are especially effective in the alkoxylation of alcohols, particularly primary alcohols such as the long-chain fatty alcohols, or mixtures thereof, which are used as starters in the manufacture of nonionic surfactants. However, heterogeneous alkoxylation catalysts incorporating the derivative can also be effectively used in the catalytic reaction of a wide variety of organic compounds containing active hydrogen. If, for example, the activator is ethylene glycol, the derivative can readily be utilized in situ to catalyze the alkoxylation of ethylene glycol itself, thereby producing ethylene glycol-started poly(oxyalkylene)glycols of any desired nominal molecular weight and advantageously having a relatively narrow molecular weight distribution.

If, by way of further example, the activator is the monoethyl ether of ethylene glycol (MEEG) and the derivative is directly alkoxylated with ethylene oxide, the product will be a mixture of ethoxylates of MEEG whose composition will be determined by the molar ratio of ethylene oxide to MEEG.

As used herein, the term "excess activator" means that amount of activator which is not chemically or physically bound to calcium and thus can be removed by simple physical means. The technique employed for this operation is not critical. Vacuum stripping is recommended for its simplicity and efficiency, but evaporation and other known procedures may also be used.

The derivative will be obtained as a finely divided, particulate solid, in slurry form, which can be readily separated from the reaction mixture by filtration, decantation, or similar procedures. The product so obtained is catalytically active in alkoxylation reactions, whether or not acid modified.

The preparation of the supported calcium catalysts of this invention requires the reaction of the catalyst precursor, e.g., aryloxy or arylthio-containing supported residues, with the calcium derivative. This particular step, referred to as the "calcium loading" or "metal loading" step, converts the aryloxy or arylthio-containing supported residue into a mixed aryl-alkyl calcium alcoholate wherein the aryl portion of the mixed alcoholate binds the calcium to the organic polymeric support and the alkyl portion of the mixed alcoholate supplies the catalytic activity to the composition. As pointed out above, this active end of the mixed alcoholate may be further modified through a partial modification with a multivalent oxyacid such as sulfuric acid, phosphoric acid and the like, or a metal salt of the multivalent oxyacid such as aluminum sulfate, zinc sulfate and the like.

Calcium loading of the functionalized resins, like the synthesis of the catalyst precursor, can be accomplished by a variety of methods known in the art. A preferred procedure which may be used to accomplish calcium loading utilizes technology described in U.S. patent application Ser. No. 621,991, filed June 22, 1984. This method involves treatment of calcium oxide or calcium hydroxide with an activator to form a calcium-containing composition which subsequently can be reacted with a catalyst precursor, e.g, the aryloxy or arylthio containing supported precursor, to produce a catalytically active, supported calcium composition of this invention which can alternatively:

1. Be used as such for alkoxylating the alcohol employed as activator for the CaO or Ca(OH)$_2$;

2. Be alcohol-exchanged prior to use for alkoxylating the alcohol used in the exchange reaction; or 3. Be partially modified with a multivalent oxyacid or metal salt thereof prior to use in either alternative #1 or #2 above.

Irrespective of the alternative selected, the heterogeneous calcium catalyst should, prior to its use, be freed of residual activator or exchanger alcohol by treatment, for example, with some inert (non active-hydrogen-containing) solvent followed by removal of the inert solvent. While not intending in any way to limit the scope of this invention to certain recovery or purification procedures, it is preferred to use ethylene glycol as activator in the preparations because it permits the removal by extraction of unbound or free calcium from the catalyst prior to use. In a particularly preferred method of catalyst preparation, the resin is loaded by reaction with CaO in ethylene glycol medium, freed of unbound alkalinity by extraction (multiple batch or continuous) with ethylene glycol, freed of excess ethylene glycol by extraction with ethylene glycol dimethylether or azeotropic distillation with toluene, and dried to remove the residual inert solvent. If this catalyst is to be alcohol-exchanged, then a similar extraction and drying procedure should be used after exchange to remove excess exchanger alcohol. If a modification step is included in the preparation, it is preferred that extraction and drying steps appropriate to the specific catalyst in question be included in the total preparative scheme. It is always preferred that the final form of the catalyst be one wherein its —X$_2$R$_3$ group be derived from the alcohol which is to be alkoxylated. This prevents production contamination via unwanted exchange reactions which can occur during alkoxylation.

It is a particularly desirable feature of this invention that the catalyst can be used to provide alkoxylate surfactants having a uniquely narrow molecular weight distribution, low pour point, and low level of unreacted starter component. In this usage, the catalyst is contacted with the starter component, e.g., alcohol under conditions at which reaction will occur, to perform an alcohol exchange (which can also be referred to as an alkoxide exchange) reaction. A portion of the starter alcohol thus is present as an alcoholate of calcium, which alcoholate is itself an active species for the alkoxylation reaction. This reaction mixture is then reacted with one or more alkylene oxides, e.g., alkylene oxides such as ethylene oxide, according to known procedures to produce the desired surfactant.

Referring now to the structural formula given above for the activator, X and Y are preferably more than one carbon removed from each other, e.g., in the beta position relative to each other, and are preferably oxygen, as in ethylene glycol, or oxygen and nitrogen, as in monoethanolamine; however, X and Y can also be sulfur or phosphorous. Exemplary of other useful compounds are ethylenediamine, N-methylethanolamine, tetrahydrofurfuryl alcohol, 2-mercaptoethanol, 1,2-propylene glycol, 2-methylthioethanol, 2-ethoxyethanol, diethylene glycol, 1,3-propanediol and 1,4-butanediol.

Z and Z' are the same or different radicals, optionally substituted, and often at least one of Z and Z' is selected from the group consisting of hydrogen, lower linear or branched alkyl of one to four carbon atoms, alkylene from two or about six carbon atoms, phenyl or lower alkyl-substituted phenyl, cycloalkyl of three to about six carbon atoms and alkylene or hetero-atom substituted alkylene rings.

In the activator, Q may comprise a carbon chain of up to six carbons between X and Y. A two- to four-carbon chain is preferred, however, because the activating capacity of X and Y is maximized at such chain lengths. Of these, a two carbon chain length is especially preferred. In highly preferred embodiments, Q will be a two-carbon chain and the structural formula will be as follows:

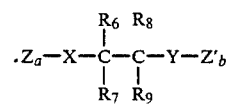

wherein Z, Z', X, Y, a and b are as defined hereinabove and R$_6$, R$_7$, R$_8$, and R$_9$ are preferably hydrogen, but may also be lower alkyl or alkylene groups of one to four carbon atoms, optionally substituted, or such other radicals as do not interfere with the usefulness of the activator for its intended purpose.

Also, Q may be cyclic, preferably cycloalkyl of six or fewer carbons, optionally substituted, as can be represented by the formula:

Compounds coming within this description would include 4-methoxycyclohexane 1,2-diol; 2-aminocyclopentanol; and 2-methoxycyclopentanol.

Similarly, either X or Y or both of them could be part of a ring structure with a carbon atom adjacent to either of them, as illustrated by the formula:

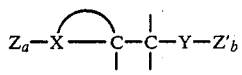

Some compounds illustrating such configurations would include tetrahydrofurfuryl alcohol; furfuryl alcohol; 2-hydroxyethyl aziridine; 1-(N methyl-2-pyrrolidinyl) ethanol; and 2-aminomethylpyrrolidine.

Moreover, X and Y can themselves be part of the same ring structure, including Q, according to the formula:

Exemplary of such compounds would be piperazine; 4-hydroxymethyl-2,2-dimethyl-1,3 dioxolane; 2,6-dimethylmorpholine; and cyclohexanone ethylene ketal.

Numerous other ring structures, whether saturated or unsaturated, substituted or unsubstituted, are also possible and are intended to be within the scope of the present invention.

The only perceived limitation on Q and on the overall structure of formula (I) is that the activator must be capable of solubilizing, at least in part, CaO and/or Ca(OH)$_2$. The solubilization of the normally insoluble CaO and Ca(OH)$_2$ is considered to be the threshold step which permits these heretofore inoperable materials to be successfully utilized. Without intending to be bound to any particular theory, this solubilization is believed to be accomplished through the electron-withdrawing effects of hetero-atoms X and Y in relation to adjacent carbon atoms, thereby increasing the acidity of the activator molecule and also helping it to participate in the formation of complexes with calcium, such as exemplified by the structure:

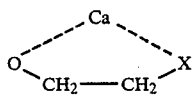

Thus, any structure represented by the formula $$Z_a-X-Q-Y-Z'_b$$

is satisfactory, provided only that it does not eliminate or neutralize the electronegativity of the hetero-atoms and thus prevent the activator from performing its intended purpose of solubilizing, at least in part, the CaO and/or Ca(OH)$_2$.

As lime is solubilized, the alkalinity of the medium increases; thus, the building of alkalinity can be used as a screening technique to identify potentially useful activators. In this test, one should look for approximately one or more grams of alkalinity, calculated as CaO, based on 5 grams of calcium (calculated as CaO) charged, as determined by titration with 0.01 N HCl in ethanol (alcoholic HCl), as will be described more fully below. It should be noted, however, that amines interfere with this test, thus, it cannot be dependably used with amine-containing activator candidates.

In the solubilizing step of the process of this invention, as has been mentioned above, CaO and/or Ca(OH)$_2$ are mixed with the activator to form one or more derivative species. The purpose of this treatment is to solubilize sufficient lime to be catalytically effective in an alkoxylation reaction; thus, the lime concentration could be either below or above its solubility maximum in the activator, provided only that sufficient lime is solubilized to be catalytically effective. As a general guideline, however, the concentration of lime used in the initial step should typically be in the range of about 1-2%, based on the activator. The lime should normally be present somewhat in excess of its solubility in the activator, but lime concentrations exceeding about 30% would rarely be considered desirable.

The temperature for this procedure is not considered critical, and can range from about 50° C. up to the boiling point of the activator, typically well over 200° C. It is desirable to operate in the range of about 90° to 150° C., preferably about 125° to 150° C., and the system can be put under either vacuum or pressure to maintain any desired temperature while maintaining the activator in the liquid phase. Advantageously, the conditions of temperature and pressure are such that water can be vaporized and removed from the reaction medium.

Preferably the catalyst preparation is conducted under a substantially inert atmosphere such as a nitrogen atmosphere.

To perform this step of the process, lime is simply added to the activator in a stirred vessel under sufficient agitation to create a slurry of the lime for a period of time adequate to solubilize at least a portion of the lime. Normally, this will be accomplished within a period of about 1 to 4 hours. The amount of lime which will be solubilized will depend, of course, on the concentration of lime present, the effectiveness of the activator used, and on the temperature, time and agitation employed. Ideally, the quantity of lime desired for the subsequent alkoxylation reaction is solubilized. The source of the lime for this step includes any commercially-available grade of quicklime or slaked lime, since the impurities typically contained in such lime do not significantly adversely affect the catalyst formed by the procedures of this invention.

The resulting lime/activator derivative is then reacted with the catalyst precursor to produce a catalyst for alkoxylation reactions (although it is preferably modified to enhance the narrowness of the alkoxylation product). This would be the case where, for example, ethylene oxide is to be added to the material used as the activator, e.g., ethylene glycol, to produce poly(oxyethylene)glycols of any desired molecular weight.

If the catalyst is to be used to produce a surfactant or other alkoxylation product using a different starter, an exchange can be performed as described above. For example, in producing a surfactant, the catalyst of formula (i) hereinabove can be added to a stirred vessel containing a surfactant range alcohol or mixture of such alcohols, typically C$_{12}$-C$_{14}$ alcohols. The concentration of derivative used can vary over a very broad range, but ideally would be approximately that desired for the subsequent alkoxylation reaction. The temperature during the exchange reaction may be any temperature at which the reaction will occur, but, preferably, will be in the range of about 200°-250° C., and pressure may be adjusted to achieve these temperatures. If the exchange procedure is followed, the activator chosen should have a boiling point of less than about 200° C. to permit it to be readily stripped from the detergent alcohol, most of which boil in the 250° C. range or higher. The resulting alcohol-exchanged product is suitable for use directly as a catalyst in alkoxylation reactions to produce surfactants started with the exchanged alcohol or alcohols although it is preferably acid modified to enhance the narrowness of the alkoxylation product.

The catalyst produced by the above-described process is often in the form of a stable slurry of finely divided (e.g., about 5 microns) particles, strongly basic (pH about 11-12), and containing excess CaO.

Although not required for alkoxylation reaction, it is highly preferred that the catalyst of formula (i) hereinabove, or the alcohol-exchanged product thereof, be partially neutralized with acid prior to use as catalyst for alkoxylation if narrower distribution of alkoxylate products is desired. While the precise chemical nature of this procedure is not fully understood, it does result in a demonstrable improvement to the overall process in that the molecular weight distribution is narrowed still further. In addition, modified catalysts tend to required little or no induction period in the alkoxylation reaction, and also increase the reaction rate over that of their unmodified counterparts. In contrast, addition of acid to conventional catalysts, such as potassium hydroxide, slows the alkoxylation rate while producing no beneficial effect on the product distribution.

Advantageous results can be obtained if the catalyst is used in its "crude" form, i.e., without separation from its reaction mixture or purification. Nevertheless, if desired, the heterogeneous catalyst, whether modified or not, can be separated from its reaction mixture, purified, dried and stored. Such may be accomplished in a straightforward manner, as by stripping off the excess activator or other organic material containing active hydrogen, filtering the resulting slurry, reslurrying the wet solids with a solvent (e.g., tetrahydrofuran) and refiltering, and drying, preferably under vacuum. The solids thus obtained will be catalytically active, but, frequently, they are substantially less active than the catalyst in its "crude" form. Reaction rate notwithstanding, however, the desired narrow molecular weight distribution and other benefits can still be obtained.

It is a highly desirable, and quite unexpected, benefit of this aspect of the invention that the overall process embodied in the various procedures described above for making catalysts from lime is remarkably "forgiving" of process variations. Thus, considerable flexibility exists as to the point modifier is added and, within reasonable limits, how much modifier is used. Similarly, the unreacted activator may be removed wholly or partially prior to, e.g., an exchange reaction, if used, or it may be left present during the exchange reaction. Moreover, the catalyst may be re-used indefinitely, used and stored in its "crude" form, or purified and dried, with any loss in reaction rate made up by increasing temperature.

The procedures involved in carrying out the process of this invention are illustrated by the following description directed toward the manufacture of nonionic surfactants.

The manner in which the process of this invention is practiced can be illustrated by the following generalized procedure for preparing a slurry of calcium alkoxylation catalyst intended for use in the manufacture of "peaked" (narrow molecular weight distribution) linear alcohol ethoxylates (nonionic surfactants).

As applied to the specific case of the production of nonionic surfactants, the process of this invention is characterized by a considerable degree of operational latitude. This is particularly true in the preferred version of the process wherein the modified form of the catalyst is produced. From the standpoint of the chemistry which takes place, there are four distinct steps in the preparation of the unmodified catalysts and five distinct steps in the preparation of the modified catalysts. Steps 1, 2, 3 and 4, which are common to the preparation of both catalyst types, involve the following reactions:

Step 1—Reaction of an organic polymer which has a crosslinked, microporous, macroporous or physically expanded structure with a carbocyclic or heterocyclic compound to produce a catalyst precursor.

Step 2—Reaction of lime (or mixtures of major quantities of lime with minor quantities of other alkaline earth bases) with a suitable activator.

Step 3—Reaction of the catalyst precursor formed in step 1 with the product formed in step 2 above.

Step 4—Reaction of the product formed in step 3 above with a detergent range alcohol to effect exchange of the activator-derived organic radicals for detergent-range alcohol-derived organic radicals.

During or following the exchange reactions of step 4 the activator, which preferably is substantially more volatile than the detergent-range alcohol, is removed from the system by distillation. At the conclusion of this operation, the unmodified version of the catalyst is obtained in the form of an activator-free slurry in the detergent-range alcohol.

In the preparation of the unmodified form of the calcium catalyst, steps 2 and 4, above, may be combined into one operation wherein the lime is reacted with a mixture of activator and detergent range alcohol. In cases where especially effective activators are being used (e.g., ethylene glycol, 1,2-propylene glycol, ethylene glycol monoethylether, etc.), this alternative procedure of combining the activator with the detergent-range alcohol is frequently preferred because it tends to minimize color build-up in the catalyst slurry. From the standpoint of the final product characteristics, both procedures are equally acceptable. Modified processes wherein the activator is fed into a slurry of the detergent-range alcohol and the calcium base or the detergent-range alcohol is fed into a slurry (or, in some cases, a solution) of the calcium base in the activator are also operationally viable, although their use offers no perceived advantage over the batch charging version.

The preparation of the modified catalyst involves a fifth major processing operation which, like that of steps 1, 2, 3 and 4, is a distinct step in terms of the chemistry which takes place.

Step 5—Treatment of the slurry of unmodified catalyst in detergent-range alcohol with a deficiency of some appropriate modifier such as polyvalent oxyacid (e.g., $H_2SO_4$, $H_3PO_4$, $H_2MoO_4$, etc.).

This step provides a highly-active, modified calcium catalyst in the form of a slurry in the detergent-range alcohol. The product slurry is normally subjected to an in vacuo drying operation before it is employed in an ethoxylation reaction to manufacture a nonionic surfactant. The modifier charge can be based either upon the initial lime charge or, more desirably where possible, upon an "active catalyst" value which is obtained by titrating a sample of the lime/activator reaction mixture for alkalinity content using 0.01 N alcoholic HCl in the presence of bromothymol blue indicator. When an inorganic oxyacid is employed, it is convenient to use the above procedure. A particularly convenient procedure is to follow the course of the lime/activator reaction by titration and to base the acid modifier charge upon the alkalinity value obtained when a constant level of alkalinity has been reached. An especially convenient and effective procedure, for example, is to add the acid modifier at a level of about 50% of this "constant" alkalinity value. Monitoring of the lime/activator reaction by titration and ultimately determining the acid modifier charge based upon this analysis, although frequently a preferred procedure, cannot be used with amino-functional activators because the amine functionality interferes with the alkalinity analysis. In such instances, the preferred procedure is to base the acid modifier charge on the alkalinity value obtained by titrating the activator-free (stripped) slurry of catalyst in detergent alcohol.

Because of the fact that this process offers such wide operational latitude, there is no single procedure which can be said to represent the general procedure. This consideration notwithstanding, one procedure which will suffice to illustrate the process is as follows:

A catalyst precursor is prepared via the Williamson etherification reaction employing a 200-400 mesh Merrifield ® Resin (2% crosslinked polystyrene chloromethylated to a level of 5 milliequivalents/gram) as the support reactant and hydroquinone as the phenolic reactant. Alternatively, the catalyst precursor is prepared by Friedel Crafts alkylation of monomethylhydroquinone with a 200-400 mesh Merrifield ® Resin of the type described above.

Lime (as commercially supplied or calcined 6 hours at 600° C.) and 2-ethoxyethanol (available from Union Carbide) are then charged to a suitably-sized, agitated vessel equipped with a reflux condenser, thermocouple, 10-tray distillation column, and inert gas purge inlet. The reactants are charged in weight ratios ranging from 60 to 80 parts of 2-ethoxyethanol to one part of lime. The charge is heated under a nitrogen purge for a period of 2 to 6 hours at the reflux temperature (about 135° C.) while refluxing solvent is removed overhead continuously or intermittently- at a make rate sufficiently slow such that during the entire reaction period only about 10 to 15% of the original solvent charge is removed overhead. The purpose of this operation is to remove from the system water which was either introduced with the reactants or produced by chemical reaction. During the reflux period, the reaction mixture is sampled at periodic intervals to monitor the buildup of "alkalinity" which is indicative of the formation of catalytically active materials. The analytical method used for this purpose is a titration with 0.01 N HCl in 2-ethoxyethanol using bromothymol blue indicator. When similar "alkalinity" levels are obtained from two successive titrations, the lime/activator reaction step is considered to be finished. The usual timed period to reach this point is about 4 hours.

The catalyst precursor is then reacted with the lime/activator product under conventional reaction conditions to afford the alkoxylation catalyst such as illustrated in the examples hereinafter.

At this point the reaction mixture is diluted with the detergent range alcohol to be ethoxylated; typically the quantity of alcohol added is about 100 grams/gram of lime (calculated as CaO) used in the initial reaction. The resulting mixture is cooled to about 75° C. and treated, under agitation, with sufficient modifier, preferably sulfuric acid, to neutralize about 50% (on an equivalents basis) of the alkalinity indicated to be present by the final titration performed on the lime/activator reaction mixture.

The temperature is then increased to permit removal of the activator from the reaction mixture by distillation at atmospheric pressure. Distillation at atmospheric pressure is continued until the kettle temperature reaches about 175 to 180° C. At this point the pressure on the system is reduced to about 180 mm Hg and stripping of the activator is continued until the kettle reaches a temperature of about 215° to 225° C. and both the kettle product and the distillate are free of activator as indicated by gas chromatographic (GC) analysis (e.g., less than 1000 ppm by weight and often less than 100 ppm by weight).

The thus-obtained activator-free slurry of catalyst in detergent alcohol can either be used directly as a charge to the ethoxylation reactor or, optionally, diluted with sufficient, dry detergent range alcohol to afford any desired catalyst concentration in the slurry. A final "alkalinity" value on this slurry may, if desired, be obtained by the same titration procedure described hereinabove.

The above procedure represents but one of many equally viable versions of this process. The runs summarized in the examples hereinafter illustrate the use of several, but by no means all, of the versions which are possible through different combinations of the options available in the various process steps.

The heterogeneous catalytic reactions of this invention can be effected, for example, by conventional methods such as (1) batch processes; (2) continuous fixed-bed processes; and (3) continuous fluidized reactor processes. In a batch reactor, the catalyst is kept suspended in the reactant by shaking or stirring. In a fluidized reactor, the catalyst is at a particular original level. As the velocity of the reactant stream is increased, the catalyst bed expands upward to a second level, and at a critical velocity it enters into violent turbulence. The fluidized reactor is particularly useful for removing or supplying the heat necessary to maintain a fixed catalyst temperature. The fluidized reactor can usually be employed only on a rather large scale since good fluidization requires a reactor larger than about 1.5 inches in diameter.

The processes of this invention broadly involve the liquid or gaseous use of heterogeneous calcium-containing catalysts for the alkoxylation of active-hydrogen compounds, preferably hydroxyl-containing compounds, such as, primary or secondary alcohols, diols or triols. Mixtures of active-hydrogen compounds can be used.

Alkoxylation product mixtures prepared by the processes of this invention comprise alkoxylation species that can be represented by the formula $$R_{10}[(CHR_{11}-CHR_{12}O)_rH]_s$$

wherein $R_{10}$ is an organic residue of an organic compound having at least one active hydrogen, s is an integer of at least 1 up to the number of active hydrogens contained by the organic compound, $R_{11}$ and $R_{12}$ may be the same or different and can be hydrogen and alkyl (including hydroxy- and halo-substituted alkyl) of, for example, 1 to 28 carbons, and r is an integer of at least 1, say, 1 to about 50.

Organic compounds having active hydrogens include alcohols (mono-, di- and polyhydric alcohols), phenols, carboxylic acids (mono , di- and polyacids), and amines (primary and secondary). Frequently, the organic compounds contain 1 carbon to about 100 or 150 carbons (in the case of polyol polymers) and can contain aliphatic and/or aromatic structures. Most often, the organic compounds are selected from the group of mono-, di- and trihydric alcohols having 1 to about 30 carbon atoms.

Particularly preferred alcohols are primary and secondary monohydric alcohols which are straight or branched chain such as methanol, ethanol, propanol, pentanol, hexanol, heptanol, octanol, nonanol, decanol, undecanol, dodecanol, tridecanol, tetradecanol, pentadecanol, hexadecanol, octadecanol, isopropyl alcohol, 2-ethylhexanol, sec-butanol, isobutanol, 2-pentanol, 3-pentanol and isodecanol. Particularly suitable alcohols are linear and branched primary alcohols (including mixtures) such as produced by the "Oxo" reaction of $C_3$ to $C_{20}$ olefins. The alcohols may also be cycloaliphatic such as cyclopentanol, cyclohexanol, cycloheptanol, cyclooctanol, as well as aromatic substituted aliphatic alcohols such as benzyl alcohol, phenylethyl alcohol, and phenylpropyl alcohol. Other aliphatic structures include 2-methoxyethanol and the like.

Phenols include alkylphenyls of up to 30 carbons such as p-methylphenol, p-ethylphenol, p-butylphenol, p-heptylphenol, p-nonylphenol, dinonylphenol and p decylphenol. The aromatic radicals may contain other substituents such as halide atoms.

Alcohols (polyols) having 2 or more hydroxyl groups, e.g., about two to six hydroxyl groups and have 2 to 30 carbons, include glycols such as ethylene glycol, propylene glycol, butylene glycol, pentylene glycol, hexylene glycol, neopentylene glycol, decylene glycol, diethylene glycol, triethylene glycol and dipropylene glycol. Other polyols include glycerine, 1,3-propanediol, pentaerythritol, galactitol, sorbitol, mannitol, erythritol, trimethylolethane and trimethylolpropane.

The alkylene oxides which provide the oxyalkylene units in the ethoxylated products include alkylene oxides such as ethylene oxide, propylene oxide, 1,2-butylene oxide, 2,3-butylene oxide, 1,2- and 2,3-pentylene oxide, cyclohexylene oxide, 1,2-hexylene oxide, 1,2-octylene oxide, and 1,2-decylene oxide; epoxidized fatty alcohols such as epoxidized soybean fatty alcohols and epoxidized linseed fatty alcohols; aromatic epoxides such as styrene oxide and 2-methylstyrene oxide; and hydroxy- and halogen-substituted alkylene oxides such as lycidol, epichlorhydrin and epibromhydrin. The preferred alkylene oxides are ethylene oxide and propylene oxide.

The selection of the organic residue and the oxyalkylene moieties is based on the particular application of the resulting alkoxylation product. Advantageously, narrow distributions can be obtained using a wide variety of compounds having active hydrogens, especially monohydric alcohols, which provide desirable surfactants. Because of the narrow distribution of the alkoxylation product mixture, especially attractive alkoxylation products are surfactants in which certain hydrophilic and lipophilic balances are sought. Hence, the organic compound often comprises a monohydric alcohol of about 8 to 20 carbons and the alkylene oxide comprises ethylene oxide.

While the processes described herein are capable of selectively providing narrow distributions of alkoxylates with the most prevalent having as low as one mole of oxyalkylene per mole of active hydrogen site, a particular advantage exists in the ability to provide a narrow distribution at higher levels of alkoxylation, e.g., wherein the most prevalent specie has at least 4 oxyalylene units. For some surfactant applications, the most prevalent alkoxylation specie has 6, 7, 8, 9, 10, 11 or 12 oxyalkylene units per active hydrogen site. For many surfactant applications, it has been found that a relatively few species provide the desired activity, i.e., a range of plus or minus two oxyalkylene units. Hence, the compositions of this invention are particularly attractive in that the range of alkoxylation is narrow, but not so narrow that a range of activity is lost.

Moreover, the relatively symmetrical distribution of alkoxylate species that can be provided by this invention enhances that balance while providing a mixture that exhibits desirable physical properties such as cloud point, freeze point, viscosity, pour point and the like. For many alkoxylation mixtures of this invention, the species falling within the range of $\bar{n}$ plus or minus two comprise at least about 75, say, about 80 to 95, sometimes 85 to 95, weight percent of the composition. Importantly, the compositions can be provided such that no single alkoxylation product is in an amount of greater than 50 weight percent of the composition, and, most often, the most prevalent specie is in an amount of 20 to about 30 weight percent, e.g., about 22 to 28, weight percent, to enhance the balance of the composition.

Another class of alkoxylation product mixtures are the poly(oxyethylene)glycols. For instance, triethylene glycol and tetraethylene glycol find application in gas dehydration, solvent extraction and in the manufacture of other chemicals and compositions. These glycols can be prepared by the ethoxylation of ethylene glycol and diethylene glycol. Advantageous processes of this invention enable ethoxylate product compositions containing at least about 80, say, about 80 to 95, weight percent of triethylene glycol and tetraethylene glycol.

Among the most commercially important alkoxylation products are those which utilize water or an alcohol (monols, glyols, polyols, etc.) as starter (initiator) and ethylene oxide, propylene oxide, or an ethylene oxide/propylene oxide mixture as the 1,2-alkylene oxide monomer. Such alcohol ethoxylates encompass a myriad of structures, compositions and molecular weights intended for service in a diversity of applications ranging from heavy duty industrial end uses such as solvents and functional fluids to ultra-sophisticated, consumer-oriented end uses such as in pharmaceutical, personal care and household goods. The supported catalysts of the instant invention find utility in the manufacture of a broad range of alkoxylation products, but are particularly useful in the manufacture of alkoxylates designed for service in sophisticated, consumer-oriented end use areas of application where product quality demands are stringent. Among the many types of alkoxylates which are used in such applications, two of the most prominent are the poly(oxyethylene)glycols and the fatty alcohol ethoxylates. The poly(oxyethylene)glycols, known under such tradenames as CARBOWAX®, POLYGLYCOL E®, PLURACOL E®, etc., are manufactured by ethoxylation of ethylene glycol or one of its homologues; they are produced over a molecular weight range of about 200 to about 8,000. The fatty alcohol ethoxylates, known under such non-ionic surfactant tradenames as NEODOL®, ALFONIC®, TERGITOL®, etc., are manufactured by ethoxylation of linear or branched $C_{10}$–$C_{16}$ saturated alcohols; they are produced over a molecular weight range of about 300 to about 800. It is in the production of these and other performance type, premium quality ethoxylates that the supported catalysts of the instant invention offer maximum advantages relative to the usual homogeneous ethoxylation catalysts (NaOH, KOH, etc.) which must be removed ultimately from the finished product.

The alkoxylation product mixtures of this invention are characterized by having a negligible amount of catalyst residues. For purposes of this invention, a negligible amount of catalyst residues is an amount sufficient to ensure shelf stability and market acceptability of the alkoxylation product; a catalyst neutralization/catalyst salt removal step is not required. Preferably, the amount of catalyst residues in the alkoxylation products of this invention is less than 0.01 milliequivalents per gram of product. Stated another way, the amount of catalyst residues in the alkoxylation product mixtures of this invention is such that a catalyst neutralization/catalyst salt removal step is not required in the processes for preparation thereof.

Conventional alkoxylation products typically contain catalyst residues which must be neutralized, at the very least, or more generally, both neutralized and removed to ensure shelf stability and market acceptability of the alkoxylate product. Neutralization/removal of such catalyst residues is a time-consuming operation which adds significantly to the cost of the finished alkoxylate product. Some of the procedures used commercially are the following:

1. Neutralization without Salts Removal—in this case, neutralization is conducted with a species, usually an acid such as acetic acid, which affords a salt that is soluble in the ethoxylate product.

2. Neutralization with Salts Removal—similar to above, but conducted with a species which affords an insoluble salt removable from the product by filtration or centrifugation; phosphoric acid is frequently used in this procedure.

3. Neutralization with Diatomaceous Earths—in this case, the ethoxylate is neutralized with a diatomaceous earth such as Magnesol ®, e.g., and the salts are removed along with the excess diatomaceous earth by filtration or centrifugation.

4. Neutralization by Ion-Exchanging—in this case, the product is diluted with a solvent and passed through a bed containing ion-exchange resin(s); the effluent from the bed is then subjected to an evaporative distillation to remove the diluent; the quality of ion-exchanged products is very high; however, both capital and operating costs of this process technique are high.

The utility of the supported alkoxylation catalysts of this invention derives from their capability to afford quality products directly, e.g., without post-treatments such as neutralization/removal. When utilized in a batch slurry reaction mode, the supported catalyst is separated from the reaction product by some simple procedure such as filtration, centrifugation, decantation, etc. In the fixed bed reaction mode, no separation whatever of supported catalyst from product is required, although a "polishing" filtration of the product may be desirable to remove spurious foreign matter and/or fine particulates which may arise through mechanical attrition of the bed packing. In batch reaction mode operation, separation of the supported catalyst from the alkoxylate product is preferably accomplished by a procedure which minimizes possible exposure of the dry or largely dry catalyst to the atmosphere. This is so..because moisture and/or carbon dioxide can be detrimental to the activity/life of the supported catalyst. Thus, for example, procedures such as centrifugation, decantation, etc., are generally preferred over filtration, particularly in case where product cross-contamination possibilities do not exist, as in cases wherein the same product is made from one batch to the next. In cases where filtration is necessary, exposure of the final filter cake (in largely dry form at this point) to atmospheric gases should be minimized as much as possible.

Elimination of a neutralization operation through the use of supported catalysts of this invention not only improves process economics, but also enhances product quality. Quality problems such as color, odor, clarity, residual metal ions, and storage stability, etc., typically have their origins in the catalyst neutralization/catalyst salts removal operations. It is significant, therefore, that product quality enhancements accrue from the use of the supported catalysts of this invention. The use of supported catalysts will likely gain increased importance because of the ever-increasing demands of emerging technologies for higher purity ("cleaner") chemical intermediates and of environmental regulatory agencies for less-polluting chemical manufacturing operations.

EXAMPLES

This invention is further illustrated by the following examples, which in no way are intended to limit the applicability or scope of the invention.

EXAMPLE 1

Part A. Preparation of Catalyst Precursor

To a stirred flask equipped with a reflux condenser and Dean-Stark trap was charged 10.11 grams of hydroquinone, 6.59 grams of potassium hydroxide (85% KOH pellets), 37.4 grams of water and 200 grams of toluene. This mixture was heated at reflux while water was removed as the bottom layer of toluene/water azeotrope. When water removal was complete, the solid suspension was filtered and the solid recovered was charged back to the same reaction flask along with 20 grams of 200–400 mesh Merrifield Resin (2% crosslinked polystyrene chlormethylated to a level of 5 milliequivalents/gram) and 200 grams of N,N dimethylformamide. The mixture was heated overnight at reflux, cooled, and filtered. The wet solids recovered (56.1 grams) were slurried in 300 grams of water (to dissolve by-product potassium chloride) and refiltered. The recovered solids were slurried again in 250 grams of ethylene glycol dimethylether (Glyme ®), refiltered, and dried in vacuo to give 24.0 grams of catalyst precursor.

Part B. Preparation of Calcium Catalysts

To a stirred reaction flask equipped with distillation head and vacuum capability was charged 5.0 grams of calcium oxide and 300 grams of ethylene glycol. The system was refluxed at 155° C./190 mm Hg pressure for 4¾ hours, during which time 26.5 grams of ethylene glycol was removed overhead; this overhead ethylene glycol contained 1.34 grams of water by analysis. At this point the flask contents were cooled to 85° C. and 22.35 grams of catalyst precursor prepared in Part A were added. Over a period of 1¾ hours 235 grams of ethylene glycol were removed overhead at 135° C./190 mm Hg pressure. The kettle charge was filtered, the filter cake washed with ethylene glycol dimethylether, and the dark brown solid dried in vacuo at 10 mm Hg pressure to give 32.0 grams of catalyst (hereinafter referred to as Catalyst A). A 2.0 gram quantity of Catalyst A in this form was used to make fifteen sequential batch preparations of a poly(oxyethylene)glycol of about 125 molecular weight. These preparations are described in Example 9 hereinafter.

A 10.0 gram portion of Catalyst A was placed in a Soxhlet extraction apparatus and extracted with 300 grams of ethylene glycol for 5 hours at 140° C./100 mm Hg pressure. The liquid extractant at the conclusion of the treatment contained, by titration, 0.42 grams of calcium oxide. The solids recovered were slurried with 200 grams of ethylene glycol dimethylether and dried in vacuo at 10 mm Hg pressure to leave 7.0 grams of dry catalyst (hereinafter referred to as Catalyst B) as a fine powdery solid. Catalyst B was used in a five run sequential batch series of preparations wherein the product was a poly(oxyethylene)glycol of about 200 molecular weight. These preparations are described in Example 9 hereinafter.

A second portion of Catalyst A was extracted in a Soxhlet extractor as described above. In this experiment, 23.2 grams of Catalyst A was extracted with 500 grams of ethylene glycol in the Soxhlet apparatus by refluxing at 155° C./190 mm Hg pressure for 5¾ hours. By titration the liquid extractant removed 1.08 grams of calcium oxide from this charge. The solids remaining were slurried in ethylene glycol dimethylether, recovered by filtration and dried in vacuo at 10 mm Hg pressure to give 13.65 grams of powdery catalyst (hereinafter referred to as Catalyst C) which contained 2.58% calcium according to analysis by the ICPE (Inductively Coupled Plasma Emission) technique. The residual chloride content in Catalyst C was only 300 ppm. Catalyst C was used to make a series of ten sequential batch preparations of a poly(oxyethylene)glycol of about 300 molecular weight by ethoxylation of diethylene glycol at about 140° C. and 20-98 psig pressure. These experiments are described in Example 9 hereinafter.

EXAMPLE 2

Part A. Preparation of Catalyst Precursor

In the manner similar to that described in Example 1, Part A, a catalyst precursor was prepared by reacting 20 grams of 200–400 mesh Merrifield Resin (2% crosslinked polystyrene chloromethylated to a level of 5 milliequivalents/gram) with the monopotassium salt of hydroquinone (obtained from 10.11 grams hydroquinone and 6.59 grams of 85% potasssium hydroxide by azeotroping off water of reaction with toluene) overnight in 200 grams of refluxing N,N-dimethylformamide (DMF) and isolating 22.4 grams of a grafted resin catalyst precursor following a recovery procedure which included the steps of water wash, ethylene glycol dimethylether wash, and vacuum drying at 140° C., 60 mm Hg pressure.

Part B. Preparation of Calcium Catalysts

The catalyst precursor prepared in Part A was calcium loaded by reacting 20.0 grams of this catalyst precursor with the reaction product obtained by treating 300 grams of ethylene glycol with 5.0 grams of calcium oxide for four hours at 151° C./180 mm Hg pressure while removing overhead 32.5 grams of wet ethylene glycol containing 2.12 grams of water. After the precursor resin had been added to the calcium oxide/ethylene glycol reaction product, the crude catalyst was concentrated by distilling off 257 grams of ethylene glycol. The viscous slurry was extracted with 306 grams of ethylene glycol at 80–85° C. (1.5 hours) and filtered to give 39.6 grams of dark brown solids. After two further extractions in the same manner followed by a treatment with ethylene glycol dimethylether and a vacuum drying at 60° C./180 mm Hg pressure, an unmodified catalyst (hereinafter referred to as Catalyst D) was obtained as a medium brown-colored solid containing 0.85% calcium by ICPE analysis.

Catalyst D was converted into an acid modified, alkoxide exchanged catalyst for surfactant preparations by treating 16.6 grams of Catalyst D with 150 grams of Alfol 1214 (a $C_{12}/C_{14}$ linear alcohol from Vista Chemical) and 0.151 grams of concentrated sulfuric acid at 25° C./45 mm Hg, distilling off 97.2 grams of Alfol at 162° C./40 mm Hg pressure, slurrying the kettle residue with 200 grams of ethylene glycol dimethylether for 30 minutes, filtering and drying the recovered solids in vacuo. The dried solid catalyst (hereinafter referred to as Catalyst E), exchanged and acid-modified, weighed 16.9 grams and contained by analysis 0.72% calcium, 0.3% sulfur, and less than 0.07% any other metallic element. Catalyst E was used to carryout a ten run sequential batch preparative series of non-ionic surfactants by ethoxylating Alfol 1214 fatty alcohol to approximately a 6.5 mol ethoxylate of cloud point of about 50° C. This series of experiments is described in Example 10 hereinafter.

Catalyst E was also used, after an azeotropic drying with toluene, as the catalyst for synthesis of some high molecular weight poly(oxyethylene)glycols by ethoxylation of a PEG-600 starter. These experiments are described in Example 10 hereinafter.

EXAMPLE 3

Part A. Preparation of Catalyst Precursor

To a stirred reaction flask equipped with gas sparger tube, reflux condenser, and thermometer was charged 20.02 grams of 200–400 mesh Merrifield Resin (2% crosslinked polystyrene chloromethylated to a level of 5 milliequivalents/gram), 131.9 grams of p-methoxyphenol, 850 milliliters of 1,2-dichloroethane and 0.12 grams of fused zinc chloride. The mixture was refluxed for 4 days, by which time HCl gas was no longer being evolved. The reaction mixture was filtered, the collected solids washed successively with 0.03 N HCl in dioxane, distilled water and methanol, and the residual solid dried at 100° C./150 mm Hg pressure. The yield was 25.6 grams of fine orange powder whose $^{13}C$ solid NMR spectrum was consistent with the expected alkylation product and which contained 3.1 milliequivalents/gram of phenolic hydroxyl functionality appearing at 143–146 ppm with respect to TMS.

Part B. Preparation of Calcium Catalyst

The catalyst precursor prepared in Part A was calcium loaded by reacting 20.01 grams of this catalyst precursor with the product formed from the reaction of 5.02 grams of calcium oxide with 300.5 grams of ethylene glycol in a manner similar to that described in Example 1, Part B. After four extractions with ethylene glycol followed by one extraction with ethylene glycol dimethylether and drying at 100° C./150 mm Hg pressure, the unmodified catalyst (hereinafter referred to as Catalyst F) was obtained in a yield of 21.1 grams. The calcium content by ICPE analysis was 2.51%.

An acid-modified, fatty alcohol-exchanged calcium catalyst (hereinafter referred to as Catalyst G) was prepared from Catalyst F by treating Catalyst F (19.53 grams) with concentrated sulfuric acid (0.400 grams) in the presence of Alfol 1214 fatty alcohol (200.8 grams) at 57° C. followed by removal overhead of 163.6 grams of distillate (ethylene glycol+Alfol 1214) at a kettle temperature of 167° C./150 mm Hg vacuum. The kettle residue from stripping was filtered, the solid extracted with ethylene glycol dimethylether and the ethylene glycol dimethylether evaporated in vacuo to leave 17.78 grams of Catalyst G as a light-colored particulate solid containing, by analysis, 2.13% calcium and 0.45% sulfur.

The acid-modified, Alfol 1214 exchanged Catalyst G was used to prepare a twenty run batch sequential series of non-ionic surfactants having cloud points of about 50° C. at an average ethylene oxide add-on of about 6.5 moles per mole of fatty alcohol. This series of preparations is described in Example 11 hereinafter.

EXAMPLE 4

Part A. Preparation of Catalyst Precursor

A catalyst precursor was prepared in a manner similar to that described in Examples 1 and 2. From 20.0 grams of Merrifield Resin there was obtained 21.3 grams of a catalyst precursor resin containing the grafted phenolic functionality. Workup of the aqueous wash from the preparation led to the recovery of 5.5 grams of potassium chloride by-product. This is 74% of the theory for complete reaction of a Merrifield Resin having 5 milliequivalents/gram of chloromethyl functionality.

Part B. Preparation of Calcium Catalyst

The catalyst precursor prepared in Part A was converted to an unmodified calcium catalyst by treating 21.3 grams of the catalyst precursor with the reaction product from 5.0 grams of calcium oxide and 300 grams of ethylene glycol in a manner similar to that described in Example 1. The slurry remaining after removal by vacuum distillation of 230 grams of ethylene glycol was slurried twice in ethylene glycol dimethylether, the solids isolated by filtration, batch-extracted twice with ethylene glycol, reslurried once again in ethylene glycol dimethylether, filtered off, and finally dried in vacuo. The yield of unmodified catalyst (hereinafter referred to as Catalyst H) was 19.7 grams; the calcium content of this catalyst was 2.95% and residual chloride content was 200 ppm. Catalyst H was used to make 5 sequential batch preparations of PEG-600 by ethoxylation of diethylene glycol starter. Two such preparative series were made, each using 4.0 grams of catalyst initially. These preparations are described in Example 12 hereinafter.

EXAMPLE 5

Part A. Description of Catalyst Precursor

Phenolic resin BJO-0930, available from Union Carbide Corporation, Danbury, Conn., is a chemically blown, cross-linked phenolic resin made from a caustic-catalyzed phenol/formaldehyde condensate. The expanded spherical beads of resin, known as "microballons", have an average bulk density of about 0.08–0.09 grams/cubic centimeter and an average size of about 60 microns (150–160 mesh). The resin is reddish-purple in color; its phenolic hydroxyl functionality is 7.8 milliequivalents/gram by $^{13}C$ solid NMR and its benzylic hydroxyl functionality is 3.45 milliequivalents/gram by the same technique. As a rough approximation, the resin contains one cross-link per each 10 aromatic rings.

Part B. Preparation of Calcium Catalyst

A mixture of 28.0 grams of calcium oxide and 1500 grams of ethylene glycol was heated with stirring for seven hours at 131–154° C./100–180 mm Hg while 705 grams of ethylene glycol was removed overhead (seven fractions) to carry-off 9.26 grams of water. At this point, 50 grams of the phenolic resin and 1.72 grams of concentrated sulfuric acid were added at 55° C. This mixture was heated for 3.75 hours at 154° C./180 mm Hg while removing overhead in three fractions another 394 grams of ethylene glycol containing 7.2 grams of water. The charge was then filtered, the cake washed with ethylene glycol, and refiltered. The wet solids thus obtained were batch-extracted 4× with 500–600 gram portions of ethylene glycol at 70° C. to remove all "free" calcium bases. The ethylene glycol wet catalyst thus obtained (315 grams) was then freed of ethylene glycol by azeotropic distillation with toluene (1000 grams) at atmospheric pressure. When the slurry was free of ethylene glycol, it was filtered, slurried with fresh toluene at 70° C., refiltered, and finally dried in vacuo at 100° C./3 mm Hg. The yield of dry catalyst (hereinafter referred to as Catalyst I) was 69.5 grams. The calcium content was 6.3% and the sulfur content 160 ppm.

Due to the fact that Catalyst I showed an unexplainably low sulfur content, a second acid-modified catalyst was prepared by re-treating Catalyst I (18.6 grams) with concentrated sulfuric acid (1.2 grams) in 228 grams of ethylene glycol at 55° C., stripping off 165.7 grams of ethylene glycol at 154° C./180 mm Hg, finally removing the remaining ethylene glycol by azeotropic distillation with toluene, filtering off the solid (38.2 grams) slurrying the solid in 200 grams of toluene at 85° C. for 2 hours, refiltering and finally drying the solid in vacuo at 125° C./50 mm Hg pressure. The dried catalyst (hereinafter referred to as Catalyst J) weighed 16.0 grams and analyzed for a calcium content of 5.9% and a sulfur content of 0.5%.

Catalyst J was used in a 5-run sequential batch series preparation of poly(oxyethylene)glycol of about 300 molecular weight (i.e., PEG-300) conducted in a 1.5 gallon circulated autoclave reactor. This series of preparations is described in Example 13 hereinafter.

EXAMPLE 6

Part A. Preparation of Catalyst Precursor

A catalyst precursor was prepared in a manner similar to that described in Examples 1 and 2; namely, via reaction of 20.0 grams of 20–60 mesh Merrifield Resin (3% crosslinked polystyrene chloromethylated to a level of 4 milliequivalents/gram) with 11.9 grams of the pre-formed monopotassium salt of hydroquinone in refluxing N,N-dimethylformamide (DMF). The yield of washed and dried grayish colored product was 20.1 grams containing 0.8 milliequivalents/gram of phenolic hydroxyl functionality by NMR analysis. The quantity of by-product potassium chloride recovered was 3.46 grams.

Part B. Preparation of Calcium Catalysts

An unmodified catalyst was prepared from the catalyst precursor in Part A by calcium loading 19.2 grams of catalyst precursor with the reaction product obtained from treatment of 5.0 grams of calcium oxide with 310 grams of ethylene glycol at 150° C./180 mm Hg under conditions wherein water-of-reaction was removed overhead by distilling off about 64 grams of ethylene glycol during the reaction period of about 4 hours. The solid catalyst was recovered by filtration, batch-extracted three time with 150-200 gram portions of ethylene glycol at 85° C., slurried with 200 grams of ethylene glycol dimethylether for 1.5 hours, and finally dried in vacuo at 110° C./5 mm Hg pressure. The dried catalyst (hereinafter referred to as Catalyst K) weighed 18.5 grams and contained 1.01% calcium by analysis. An 8.0 gram portion of Catalyst K was used to make 2 batch preparations of poly(oxyethylene)glycol of about 300 molecular weight from ethylene glycol starter in a 1-liter stirred autoclave. These two runs are described in Example 14 hereinafter.

A second 8.0 gram portion of Catalyst K was fatty alcohol-exchanged with 220 grams of Alfol 1214 ($C_{12}/C_{14}$ linear, primary alcohol from Vista Chemical) to prepare an unmodified catalyst for use in surfactant synthesis. The exchange was carried out by distilling Alfol 1214 off overhead (carrying the exchanged ethylene glycol along with it) until the kettle temperature reached 208° C. at 75 mm Hg pressure. The residue (hereinafter referred to as Catalyst L) used for surfactant preparation consisted of a slurry of 8.0 grams of exchanged catalyst in 81 grams of Alfol 1214. This residue was used to prepare the first run in a series of four sequential batch surfactant preparations. For runs 2-4 of the series, the catalyst used was that obtained by filtering in vacuo the previous run. Thus, the catalyst itself was invariably wet with reaction product of the previous batch. These runs are described in Example 14 hereinafter.

EXAMPLE 7

Part A. Preparation of Catalyst Precursor

Friedel-Crafts alkylation of p-chlorophenol (137.5 grams) with 20.1 grams of 20-60 mesh Merrifield Resin (3% crosslinked polystyrene chloromethylated to a level of 4 milliequivalents/gram) was accomplished by refluxing for 96 hours in 1,2-dichloroethane (100 milliliters) containing 0.13 grams of fused zinc chloride. The precursor product was recovered by successive washes (200 milliliters each) with 0.03 N HCl in dioxane, distilled water and methanol followed by drying in vacuo. The dry catalyst precursor product weighed 25.8 grams and exhibited an NMR spectra consistent with the expected structure.

Part B. Preparation of Calcium Catalyst

An unmodified calcium catalyst was prepared from the catalyst precursor prepared in Part A by calcium loading of the precursor in a manner similar to that described previously. Thus the resin (36.8 grams wet with ethylene glycol) was treated for 4 hours with the reaction product from 5.1 grams of calcium oxide and 306.8 grams of ethylene glycol at 148° C./140 mm Hg under conditions wherein ethylene glycol was continuously fed into the system to replace that removed overhead along with water of reaction. After removal of the majority of the remaining ethylene glycol by distillation, the kettle residue was filtered and the solids recovered were subsequently batch-extracted 4 times with 150 milliliter portions of ethylene glycol at 70-80° C. Finally, the ethylene glycol-wet solids were slurried in ethylene glycol dimethylether, filtered and dried in vacuo to afford the unmodified calcium catalyst (hereinafter referred to as Catalyst M); the weight was 24.3 grams and the calcium content was 3.81%. Catalyst M was used for the preparation of poly(oxyethlene)glycols of about 300 molecular weight from diethylene glycol initiator.

A portion of the above unmodified Catalyst M was converted to acid-modified catalyst by treating 11.1 grams of Catalyst M with 0.45 grams of concentrated sulfuric acid in 101 grams of ethylene glycol for 2 hours at 80-90° C. followed by azeotropically distilling-off the ethylene glycol with 151 grams of toluene at reflux. The ethylene glycol-free resin was recovered by filtration, rinsed with additional toluene, and dried in vacuo at room temperature. The yield of modified catalyst hereinafter referred to as Catalyst N) was 10.0 grams of yellow powdery solid analyzing for 3.99% calcium. This form of the catalyst was also used to prepare poly-(oxyethylene)glycols of about 300 molecular weight. Both series of poly(oxyethylene)glycol runs are described in Example 15 hereinafter.

EXAMPLE 8

Part A. Preparation of Catalyst Precursor

In a manner similar to that described in Example 3, 132.2 grams of p-methoxyphenol was Friedel-Crafts alkylated with 20.1 grams of 200-400 mesh Merrifield Resin (2% crosslinked polystyrene chloromethylated to a level of 5 milliequivalents/gram). 1,2-Di-chloroethane (850 milliliters) was used as the reaction solvent and fused zinc chloride (0.1 grams) was used as catalyst; reaction time was 4 days. The washed and dried precursor resin weighed 25.6 grams and contained 3.2 milliequivalents/gram of phenolic hydroxyl functionality by NMR.

Part B. Preparation of Calcium Catalyst

An unmodified calcium catalyst was prepared from the catalyst precursor prepared in Part A by treating 20.0 grams of the precursor with the reaction product from 5.01 grams of calcium oxide and 301 grams of ethylene glycol. The reaction between the precursor and calcium oxide/ethylene glycol product was carried out at 153° C./180 mm Hg pressure with removal during 3½ hours of 103 grams of ethylene glycol overhead. Workup of the catalyst product by filtration followed by five batch extractions with ethylene glycol (80-90° C.) and then by a final washing with ethylene glycol dimethylether and drying in vacuo afforded a 20.6 grams of reddish-brown solid (hereinafter referred to as Catalyst O) containing 1.9% calcium by ICPE analysis.

A 9.0 gram portion of unmodified Catalyst O was converted to an acid-modified catalyst by treatment with 0.21 grams of concentrated sulfuric acid in 100.2 grams of ethylene glycol at 47° C. followed by removal overhead (129° C. vapor temperature/150 mm Hg pressure) of ethylene glycol (about 157 grams total in seven fractions) containing water-of-reaction (1.57 grams) and then by filtration, ethylene glycol dimethylether washing and finally drying in vacuo. The acid-modified catalyst (hereinafter referred to as Catalyst P) weighed 8.3 grams and analyzed for 1.37% calcium and 0.4% sulfur. This catalyst was used for an 8-run sequential batch series of poly(oxyethylene)glycol preparations. This series is described in Fxample 16 hereinafter.

EXAMPLE 9

Figure 5:
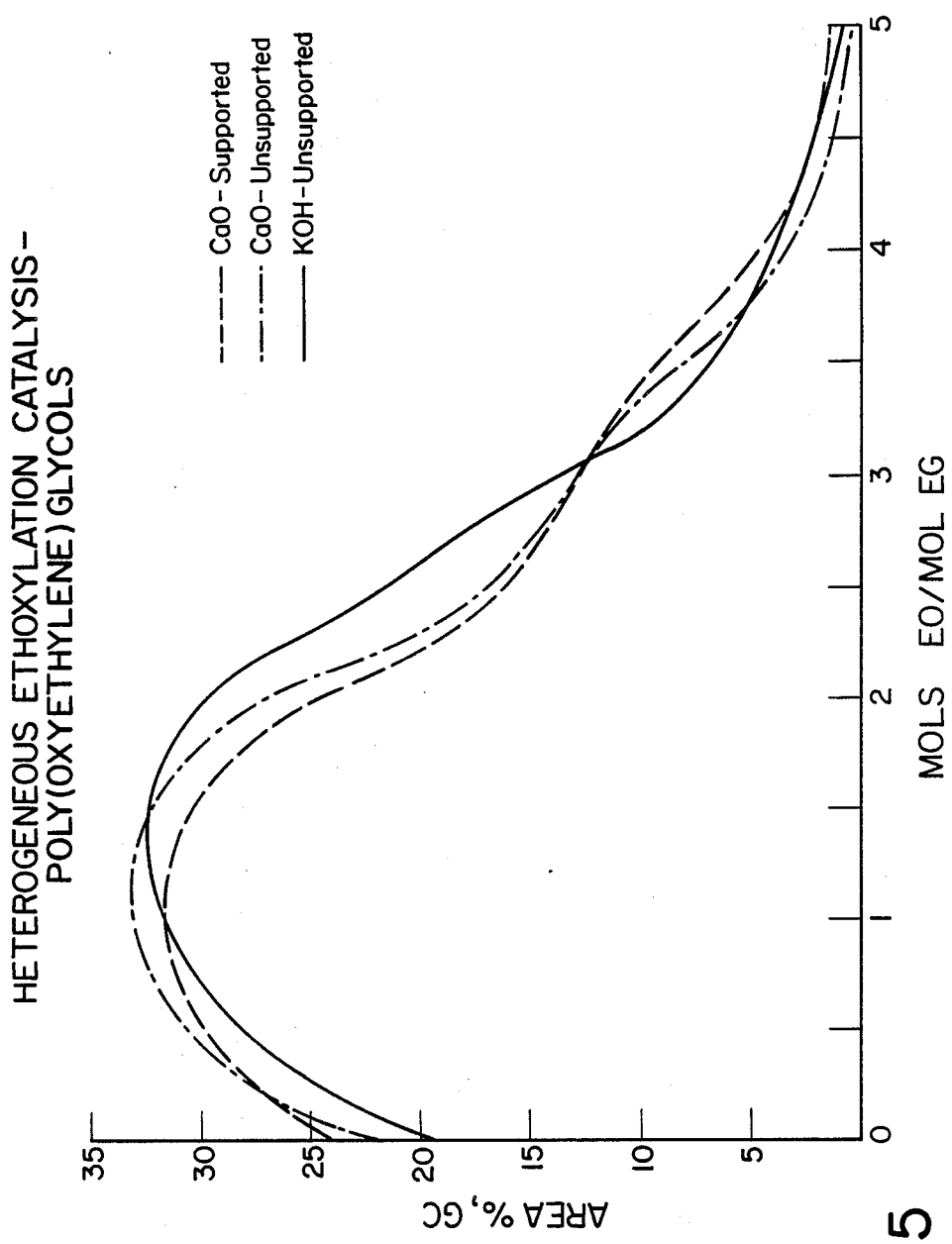
FIG. 5 depicts the average ethoxylate distribution for poly(oxyethylene)glycols prepared in Example 9, Part A, hereinafter (supported CaO) as well as unsupported KOH and unsupported CaO. The average ethoxylate distributions were obtained by averaging (area % values) individual gas chromatography scans.

Part A. Preparation of Poly(oxyethylene)glycols of about 125 Molecular Weight The catalyst used for this preparation was Catalyst A. A series of 15 sequential batch preparations was made with the centrifuged catalyst being recycled each time to the next batch; the standard charge of ethylene glycol (EG) was 40.0 grams for each batch and the target quantity of ethylene oxide (EO) to be fed was also 40.0 grams/batch. The reactor used was a 300 milliliter stirred autoclave (PARR REACTOR) which was operated at 140° C. and about 20–110 psig; ethylene oxide was fed incrementally from a pressurized ($N_2$) stainless steel tank mounted atop a Mettler balance so that the weight of ethylene oxide fed was determined by the weight decrease in the feed tank. Details for these preparations and data characterizing the products are given in Table I below. FIG. 5 depicts the average ethoxylate distribution for poly(oxyethylene)glycols prepared in this example (supported CaO) as well as unsupported KOH and unsupported CaO.

TABLE I

| | RUN NO. IN SERIES | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| PREPARATIONS REACTANT WEIGHTS, g | | | | | | | | | | | | | | | |
| Ethylene Glycol | 40.0 | 40.0 | 40.0 | 40.0 | 40.0 | 40.0 | 40.0 | 40.0 | 40.6 | 40.0 | 40.0 | 40.0 | 40.0 | 40.0 | 40.0 |
| Catalyst[a] | 2.0 | 5.2 | 5.4 | 6.0 | 4.4 | 2.2 | 3.7 | 2.5 | 4.8 | 3.1 | 3.1 | 2.9 | 2.6 | 3.1 | 2.4 |
| Ethylene Oxide[b] | 40.0 | 40.4 | 40.0 | 40.0 | 40.0 | 40.0 | 40.0 | 40.0 | 40.0 | 40.8 | 40.0 | 40.0 | 40.0 | 40.0 | 40.1 |
| | (38.5) | (31.6) | (41.7) | (35.7) | (37.8) | (40.0) | (37.0) | (38.8) | (38.4) | (41.6) | (39.9) | (45.3) | (40.8) | (40.7) | (39.1) |
| REACTION TIME, HRS.[c] | 1.7 | 5.5 | 10.0 | 11.0 | 11.5 | 12.7 | 12.7 | 12.8 | 13.2 | 14.2 | ~14 | ~14 | ~13.5 | ~13.5 | ~13 |
| PRODUCT WEIGHT, g | 80.5 | 76.8 | 87.1 | 81.7 | 82.2 | 82.2 | 80.7 | 81.3 | 83.8 | 84.7 | 83.0 | 88.2 | 83.4 | 83.8 | 81.6 |
| MATERIAL BALANCE, % | 98.2 | 89.7 | 102.0 | 95.0 | 97.4 | 96.8 | 96.4 | 98.5 | 98.1 | 101.2 | 99.9 | 106.4 | 101.0 | 100.9 | 98.9 |
| CHARACTERIZATION | | | | | | | | | | | | | | | |
| Mols EO Added/Mol EG | 1.465 | 1.415 | 1.24 | 1.21 | 1.315 | 1.24 | 1.275 | 1.37 | 1.34 | 1.40 | 1.33 | 1.53 | 1.335 | 1.37 | 1.385 |
| Hydroxyl Number, mg KOH/g | 442.8 | 451 | 480.7 | 486.1 | 467.9 | 481.6 | 474.6 | 458.0 | 463.6 | 454.3 | 466.0 | 433.5 | 464.4 | 458.7 | 456.1 |
| Alkalinity, % as CaO[d] | 0.037 | 0.006 | 0.0004 | nil | nil | nil | nil | nil | nil | nil | nil | nil | nil | nil | nil |
| Molecular Weight | 126.7 | 124.4 | 116.7 | 115.4 | 119.9 | 116.5 | 118.2 | 122.5 | 121.0 | 123.5 | 120.4 | 129.4 | 120.8 | 122.3 | 123.0 |
| pH, 5% Aqueous Sol'n | 10.7 | 9.0 | 6.2 | 5.9 | 5.8 | 5.7 | 5.4 | 5.3 | 5.4 | 5.4 | 5.7 | 5.3 | 5.5 | 6.1 | 5.9 |
| Unreacted Ethylene Glycol Content, Wt. %[e] | 16.1 | 16.9 | 25.5 | 23.6 | 25.9 | 23.9 | 24.3 | 22.4 | 22.9 | — | 21.3 | 18.1 | 21.5 | 21.4 | 20.6 |
| ETHOXYLATE DISTRIBUTION, AREA %[f] | | | | | | | | | | | | | | | |
| Ethylene Glycol | 18.8 | 19.0 | 27.2 | 27.0 | 27.3 | 26.0 | 25.0 | 25.0 | 25.8 | 23.3 | 25.5 | 21.7 | 24.4 | 23.5 | 24.7 |
| Diethylene Glycol | 30.3 | 34.8 | 30.8 | 32.4 | 35.1 | 33.1 | 31.8 | 31.2 | 32.5 | 30.8 | 31.2 | 28.9 | 31.3 | 30.3 | 29.4 |
| Triethylene Glycol | 28.9 | 28.8 | 25.7 | 24.5 | 22.6 | 24.2 | 24.6 | 24.3 | 23.5 | 24.7 | 23.8 | 25.4 | 24.7 | 23.9 | 23.5 |
| Tetraethylene Glycol | 16.1 | 12.8 | 12.2 | 11.6 | 10.6 | 11.7 | 12.7 | 12.5 | 12.3 | 13.8 | 12.8 | 15.2 | 13.1 | 13.8 | 13.6 |
| Pentaethylene Glycol | 4.8 | 3.9 | 3.5 | 3.7 | 3.6 | 4.0 | 4.6 | 4.7 | 4.7 | 5.6 | 5.1 | 6.6 | 5.0 | 5.6 | 5.6 |
| Hexaethylene Glycol | 0.9 | 0.7 | 0.6 | 0.8 | 0.9 | 1.1 | 1.3 | 1.3 | 1.1 | 1.8 | 1.6 | 2.2 | 1.5 | 2.0 | 2.2 |

[a] Catalyst weight for Run #1 is dry resin; for all runs thereafter, weight includes liquids absorbed on resin.
[b] Ethylene oxide weight is that indicated by balance to have been removed from feed tank. Value in parentheses is weight calculated by subtracting ethylene glycol and catalyst charge weight from final product weight.
[c] Reaction times are only approximate for runs 3–15 because the system ran unattended during final cook-out.
[d] by titration with 0.01 N alcoholic HCl using bromothymol blue indicator.
[e] by gas chromatography using an n-decanol internal standard with OV-101 column on Regisil-derivatized sample.
[f] by gas chromatography using an OV-101 column on Regisil-derivatized sample.

Figure 3:
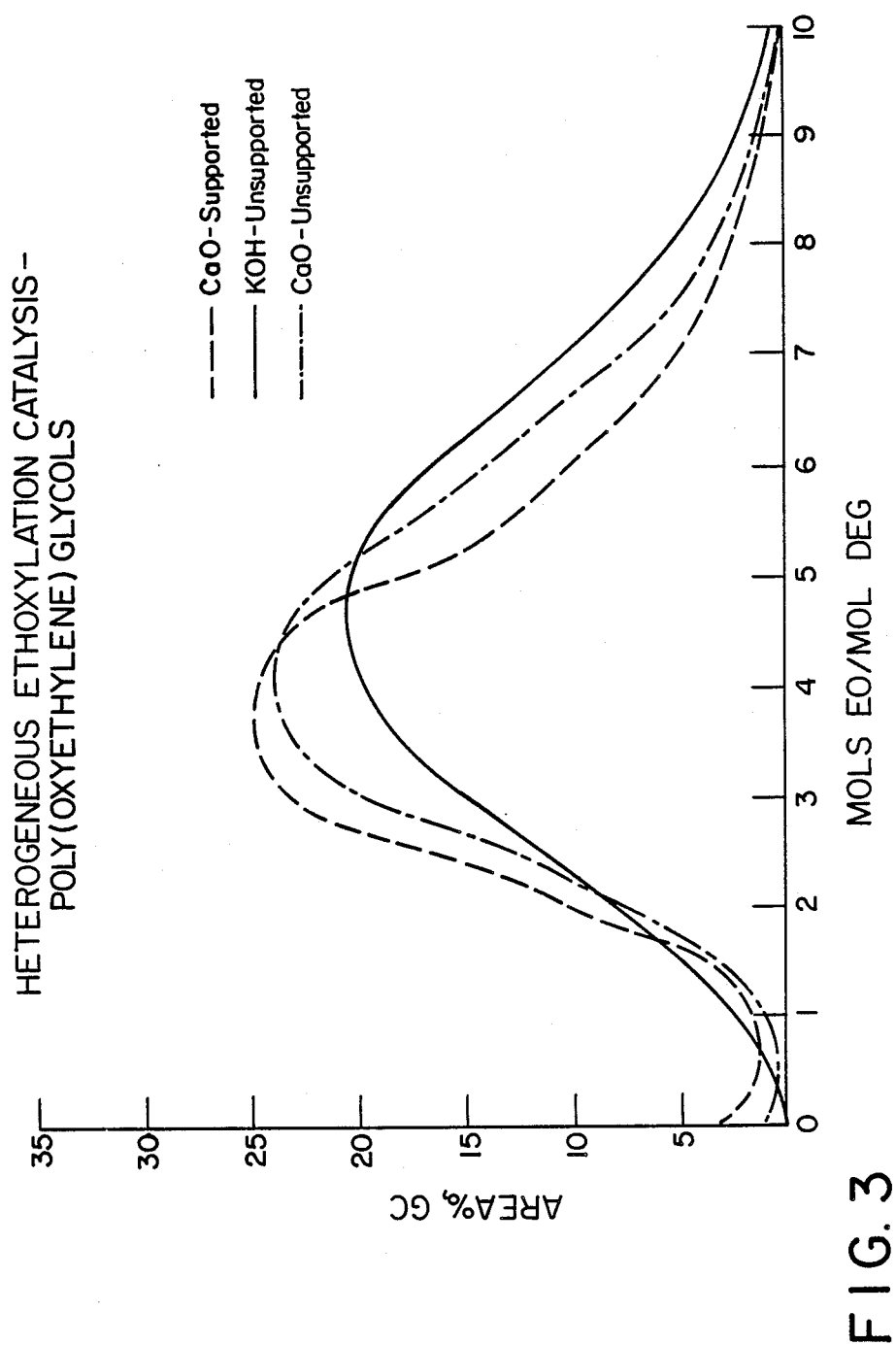
FIG. 3 depicts the average ethoxylate distribution for poly(oxyethylene)glycols prepared in Example 9, Part B, hereinafter (supported CaO) as well as unsupported KOH and unsupported CaO. The average ethoxylate distributions were obtained by averaging (area % values) individual gas chromatography scans.

Part B. Preparation of Poly(oxYethylene)glycols of about 300 Molecular Weight The catalyst for these preparations was Catalyst C, an extracted, washed and dried version of Catalyst A. Catalyst C was used to make a 10-run sequential batch series of poly(oxyethylene)glycol preparations using diethylene glycol (DEG) as initiator and the same equipment and catalyst recovery/recycle procedure as described in Part A above. In this case, standard target charges for each batch were 40.0 grams of diethylene glycol and 73.2 grams of ethylene oxide. Experimental details for these preparations and product characterization data are presented in Table II below. FIG. 3 depicts the average ethoxylate distribution for poly(oxyethylene)glycols prepared in this example supported CaO) as well as unsupported KOH and unsupported CaO.

Part C. Preparation of pOly(oxyethylene)glycols of about 200 Molecular Weight The catalyst for these preparations was Catalyst B, another glycol extracted version of Catalyst A. The poly(oxyethylene)glycol preparations comprised a sequential series of 5-runs wherein ethylene lycol was used as initiator and a 1.5 gallon circulated autoclave as reactor. Ethylene oxide feed to this reactor was motor-valve controlled, the oxide being introduced as necessary to maintain about 60 psig pressure. A standard ethylene glycol initiator charge was about 500 grams; this charge requires about 1100 grams of ethylene oxide to advance the molecular weight to 200. The catalyst charge was 7.0 grams of a 2.02% calcium containing resin; catalyst was recovered by centrifugation and recycled without cleanup or supplementation by fresh catalyst. This run series is summarized in Table III

TABLE II

| NO. OF RUNS | 10[a] | 1 | 1 | 1 |
|---|---|---|---|---|
| CATALYST TYPE | Supp. CaO (Catalyst C) | Non-supp. KOH | Non-supp. CaO | Non-supp. KOH |
| CATALYST CONC., % ON STARTER | 0.19 | 0.23 | 0.25 | — |
| REACTION TIME, HRS.[b] | ~15[c] | 0.53[d] | 4.7 | — |
| PRODUCT CHARACTERIZATION | | | | |
| Mols EO/Mol DEG | 4.15 | 4.595 | 4.425 | 4.39 |
| Hydroxyl No. mg KOH/g | 389.4 | 363.9 | 372.8 | 374.2 |
| Molecular Weight | 288.1 | 307.3 | 300.9 | 299.0 |
| Alkalinity, meg/g | 0.001[e] | 0.008 | 0.022 | n/a |
| Unreacted DEG, wt % | 1.63 | <0.1 | 0.34 | <0.1 |
| ETHOXYLATE DISTRIBUTION, AREA % | | | | |
| Diethylene Glycol | 3.22 | ~0.1 | 0.67 | <0.1 |
| Triethylene Glycol | 1.33 | 2.40 | 0.54 | 2.81 |
| Tetraethylene Glycol | 9.92 | 8.51 | 8.36 | 10.1 |
| Pentaethylene Glycol | 23.03 | 14.82 | 19.13 | 16.86 |
| Hexaethylene Glycol | 24.89 | 18.40 | 24.08 | 20.05 |
| Heptaethylene Glycol | 18.14 | 20.27 | 21.06 | 20.01 |
| Octaethylene Glycol | 10.34 | 16.55 | 14.11 | 14.85 |
| Nonaethylene Glycol | 5.23 | 10.67 | 7.58 | 8.90 |
| Decaethylene Glycol | 2.49 | 5.54 | 3.25 | 4.32 |
| Undecaethylene Glycol | 1.0 | 2.24 | 0.96 | 1.67 |
| Dodecaethylene Glycol | 0.23 | 0.60 | 0.15 | 0.44 |

Figure 4:
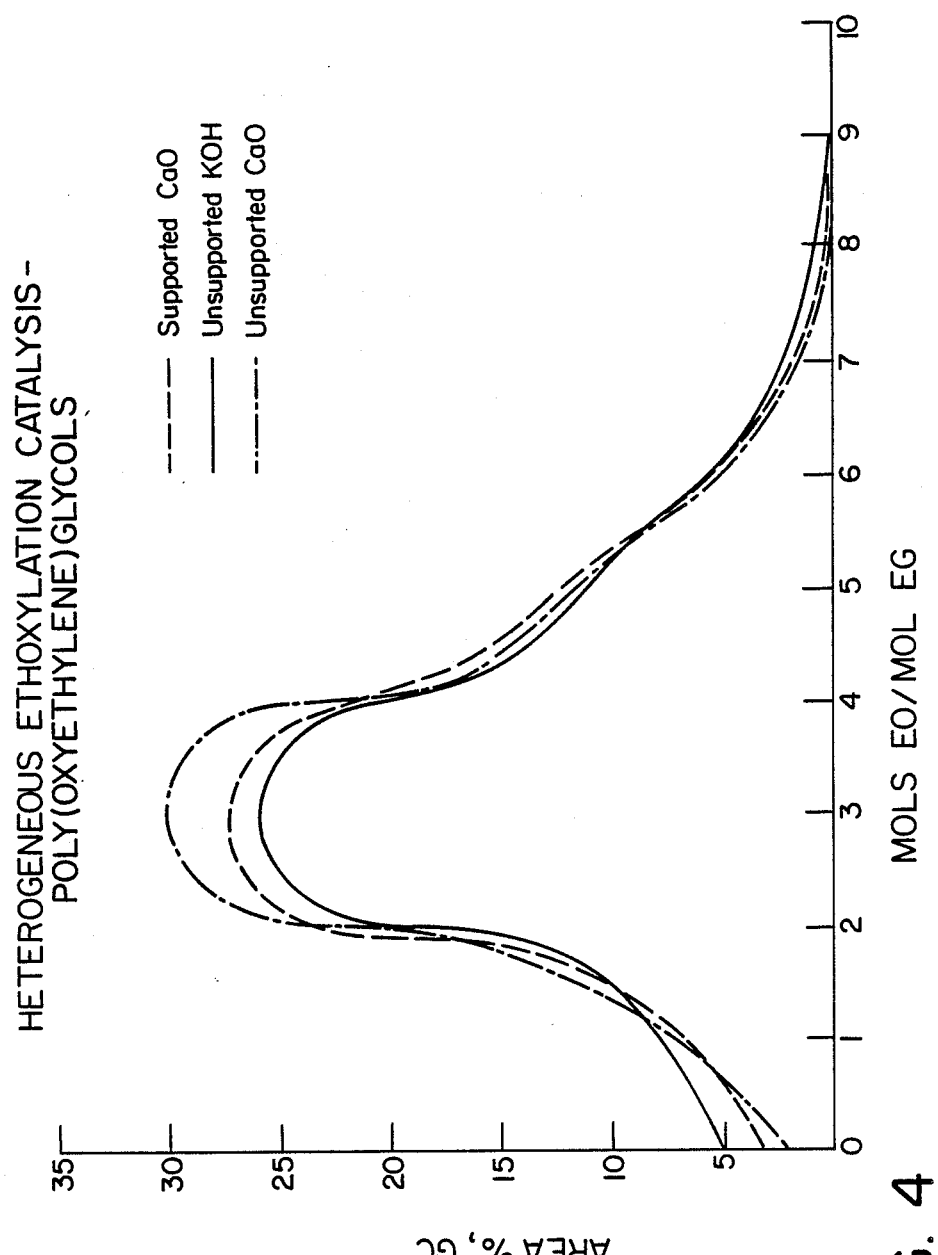
FIG. 4 depicts the average ethoxylate distribution for poly(oxyethylene)glycols prepared in Example 9, Part C, hereinafter (supported CaO) as well as unsupported KOH and unsupported CaO. The average ethoxylate distributions were obtained by averaging (area % values) individual gas chromatography scans.

[a]Average values for the 10 runs comprising the series unless otherwise noted.
[b]Reaction times are approximate for supported catalyst runs.
[c]Approximate average for runs 3–6, considered "normal" runs because of absence of "free" alkalinity and reactor operational problems.
[d]Reaction was strongly exothermic, so that average temperature was considerably greater than 140° C.
[e]Reflects residual alkalinity which was removed after first two passes.

below. FIG. 4 depicts the average ethoxylate distribution for poly(oxyethylene)glycols prepared in this example (supported CaO) as well as unsupported KOH and unsupported CaO.

TABLE III

| | RUN NO. IN SERIES[a] | | | | |
|---|---|---|---|---|---|
| PREPARATION | 1 | 2 | 3 | 4 | 5 |
| REACTANT WEIGHTS, g. | | | | | |
| Ethylene Glycol | 500 | 500 | 507.5 | 460 | 458 |
| Catalyst[b] | 7.0 | 9.5 | 7.85 | 14.0 | 21.4 |
| Ethylene Oxide | 1114 | 1116 | 1137 | 1056 | 1068 |
| REACTION TEMP., °C.[c] | 139–141 | 139–150 | 138–150 | 138–150 | 138–151 |
| REACTION TIME, HRS.[d] | 4.0 | 9.0 | 46.5[e] | 28.3 | 37.7 |
| WEIGHT OF PRODUCT, g. | 1560 | 1542 | 1533 | 1452 | 1477 |
| MATERIAL BALANCE, % | 96.2 | 94.9 | 92.8 | 94.9 | 95.5 |
| CHARACTERIZATION | | | | | |
| Mols EO Added/Mol EG | 3.05 | 3.06 | 3.075 | 3.205 | 3.405 |
| Hydroxyl No., mgKOH/g | 571.0 | 570.6 | 567.8 | 552.4 | 529.4 |
| Alkalinity, % as CaO[f] | 0.0063 | 0.0014 | nil | nil | nil |
| Molecular Weight | 196.5 | 196.6 | 197.4 | 203.1 | 211.9 |
| pH, 5% Aqueous Sol'n. | 6.4 | 6.0 | 5.1 | 5.2 | 5.2 |
| Unreacted Ethylene Glycol,[g] Content, Weight % | 1.58 | 2.16 | 2.72 | 3.36 | 1.20 |
| ETHOXYLATE DISTRIBUTION, AREA %[h] | | | | | |
| Ethylene | 2.31 | 2.79 | 4.17 | 5.62 | 2.25 |

TABLE III-continued

|  | RUN NO. IN SERIES[a] | | | | |
|---|---|---|---|---|---|
| PREPARATION | 1 | 2 | 3 | 4 | 5 |
| Diethylene Glycol | 6.51 | 6.87 | 7.78 | 5.73 | 6.75 |
| Triethylene Glycol | 21.44 | 21.10 | 20.80 | 20.24 | 21.04 |
| Tetraethylene Glycol | 29.25 | 28.70 | 26.95 | 26.29 | 25.83 |
| Pentaethylene Glycol | 21.76 | 21.72 | 21.04 | 20.70 | 20.41 |
| Hexaethylene Glycol | 11.92 | 12.12 | 12.04 | 12.64 | 12.96 |
| Heptaethylene Glycol | 5.05 | 5.12 | 5.45 | 6.11 | 6.67 |
| Octaethylene Glycol | 1.61 | 1.51 | 1.78 | 2.26 | 2.86 |
| Nonaethylene Glycol | 0.16 | 0.08 | <0.1 | 0.40 | 0.99 |
| Decaethylene Glycol | — | — | — | — | 0.24 |

[a]Runs in this series carried out in a circulated loop reactor.
[b]Catalyst weight for run #1 is dry resin; for all runs thereafter, weight includes liquids absorbed in resin.
[c]Temperatures of 140° C. were used as necessary to increase reaction rate.
[d]Reaction times are approximate for runs 2–5 made partially under non-attended conditions.
[e]Time is not accurate; mechanical problems caused delays.
[f]By titration with .01 N alcoholic HCl using bromothymol blue indicator.
[g]By gas chromatography using n-decanol internal standard with OV-101 column on Regisil ®-derivatized sample.
[h]By gas chromatography using OV-101 column on Regisil ®-derivatized sample.

EXAMPLE 10

Part A. Preparation of Fatty Alcohol Ethoxylates

A series of 10 sequential batch preparations of $C_{12}/C_{14}$ primary alcohol ethoxylates was made in a 600 milliliter stirred autoclave (a system similar to that in Parts A and B of Example 9). Following each run the catalyst, i.e., Catalyst E, was recovered by centrifugation and recycled without further treatment. Standard charge of $C_{12}/C_{14}$ primary alcohol initiator (mole wt. 202) was 40.0 grams; target ethylene oxide quantity was 6.5 moles/moles initiator, but usual practice was to introduce sufficient ethylene oxide to give an ethoxylate of cloud point of about 45–55° C. The run series was started with 8.0 grams of Catalyst E, but this quantity increased throughout the series as product absorbed on the resin. At the completion of the series of runs, Catalyst E was extracted 4× with ethylene glycol dimethylether to remove this absorbed product; the final catalyst weight after this treatment was about 22 grams. Experimental conditions for these runs and product characterization data are presented in Table IV below.

TABLE IV

|  | RUN NO. IN SERIES | | | | | | | | | |
|---|---|---|---|---|---|---|---|---|---|---|
| PREPARATION | 1 | 2 | 3 | 4 | 5 | 6 | 7 | 8 | 9 | 10 |
| Reactant Weights, g. | | | | | | | | | | |
| Alfol 1214[a] | 40.0 | 40.0 | 40.4 | 40.0 | 40.0 | 40.0 | 40.0 | 40.0 | 40.0 | 40.2 |
| Catalyst[b] | 8.0 | 21.3 | 28.3 | 36.2 | 44.2 | 44.1 | 48.3 | 51.7 | 53.2 | 53.5 |
| Ethylene Oxide[c] | 57.0 | 77.5 | 69.3 | 73.2 | 62.0 | 68.2 | 70.1 | 66.0 | 65.0 | 66.7 |
| Temperature, °C. | 139–142 | 139–141 | 140–141 | 140 | 140–142 | 139–140 | 140–142 | 140 | 138–142 | 139–140 |
| Pressure, psig | 10–80 | 8–82 | 10–74 | 10–68 | 12–80 | 11–80 | 11–72 | 10–78 | 12–80 | 10–74 |
| Reaction time, hrs.[d] | 7.25 | 14.5 | ~14 | 14.6 | 12.3 | ~12 | 15.5 | 15.2 | ~12 | 13 |
| Product Weight, g. | 102.6 | 134.7 | 138.8 | 142.4 | 143.0 | 149.4 | 155.0 | 157.0 | 155.6 | 160.6 |
| Material Balance, %[e] | 97.7 | 97.0 | 100.6 | 95.3 | 97.8 | 98.1 | 97.9 | 99.6 | 98.4 | 100.1 |
| Product Characterization | | | | | | | | | | |
| Appearance, 22° C.[k] | sl. liq. | sl. sol | wax | wax | wax | sl. sol. | wax | sl. sol. | wax | wax |
| Molecular Weight, (by OH No.) | 411.6 | 525.1 | 527.6 | 492.0 | 484.6 | 481.2 | 524.5 | 513.9 | 501.2 | 493.8 |
| Mols EO/Mol Alfol 1214[j] | 4.77 | 7.34 | 7.40 | 6.59 | 6.43 | 6.34 | 7.33 | 7.09 | 6.79 | 6.64 |
| Alkalinity, % as CaO[f] | 0.0093 | nil | nil | nil | nil | nil | nil | nil | nil | nil |
| pH, 5% Aqueous Solution | 7.7 | 6.85 | 6.9 | 6.8 | 6.9 | 6.8 | 6.9 | 6.8 | 6.9 | 6.9 |
| Cloud Point, °C. (1% sol'n.) | <20 | 55 | 57 | 55.5 | 46 | 53.5 | 54 | 53 | 48 | 45 |
| Unreacted Alcohol, wt. %[g] | 4.45 | 1.9 | 1.3 | 1.0 | 1.4 | 1.0 | 0.9 | 1.0 | 0.95 | 0.9 |
| Ether Insolubles, wt. %[h] | 9.8 | 7.2 | 8.0 | 8.3 | 7.6 | 8.1 | 9.4 | 8.8 | 10.8 | 10.6 |
| Major Component,[i] Area % | 5 EO | 7 EO | 6,7 EO | 6 EO | 6 EO | 6 EO | 6 EO | 6 EO | 6 EO | 5 EO |
| $C_{12\text{-}6}$–$C_{14\text{-}7}$, Area % | 28.4 | 30.9 | 33.9 | 35.5 | 31.7 | 35.8 | 33.4 | 33.6 | 32.1 | 31.1 |
| $C_{12\text{-}5}$–$C_{14\text{-}8}$, Area % | 52.6 | 56.2 | 60.2 | 62.7 | 58.4 | 63.6 | 60.6 | 60.3 | 59.6 | 58.6 |
| Calcium Content, ppm | 21 | 15 | 18 | 17 | 14 | 12.5 | 12 | 12 | 11 | 11 |
| Total Metals Content, ppm | ~34 |  | ~25 |  | ~19 |  | ~18 |  | ~17 |  |

[a]Alfol 1214 is a Conoco (Vista Chemical) $C_{12}/C_{14}$ linear primary alcohol of about 202 molecular weight - water content is 0.04%.
[b]Catalyst was Catalyst E, an acid-modified version of hydroquinone - grafted catalyst. The gain in catalyst charge following run #1 represents material absorbed on resin.
[c]Weight of EO indicated to have been fed based upon weight loss in feed tank.
[d]Reaction times are approximate and do not include overnight cook-down times.
[e]No corrections made for weight losses resulting from sample removal(s).
[f]By titration with 0.01N alcoholic HCl in CELLOSOLVE using bromothymol blue indicator.
[g]Gas chromatography determination on Regisil ® - derivatized sample using n-decanol as internal standard; SP-2100 column.
[h]By extracting 25 grams of product with 250 grams ether at 25° C.
[i]Gas chromatography determination using Regisil ® - derivatized sample; SP-2100 column.
[j]Theoretical quantity only of ethylene oxide was fed; no attempt was made to increase feed to obtain a 50° C. cloud point.
[k]Sl. = slushy; liq. = liquid; sol. = solid.

Part B. Preparation of High Molecular Weight Poly(oxyethylene)glycols

Catalyst E used above in Part A for the preparation of $C_{12}C_{14}$ primary alcohol ethoxylates was also used to prepare some high molecular weight poly(oxyethylene)glycols. The reactor system employed for this work was that described in Part A above; namely, a 600 milliliter stirred autoclave equipped with an internal cooling coil. Three runs were made with poly(oxyethylene)glycol of about 600 molecular weight as initiator; the molecular weights attained in these runs were 2432, 3501 and 4083, respectively. The catalyst for each run was that recovered from the previous run after isolation by filtration of the solvent-diluted product and drying in vacuo. The initial catalyst charge was 3.5 grams. The reaction products were taken up in solvents out of necessity because these poly(oxyethylene)glycols are solids at ordinary temperatures. Conditions for these preparations and product characterization data are presented in Table V below. The fourth tabulated run, i.e. Run No. 4, represents an unsuccessful attempt to prepare a poly(oxyethylene)glycol of greater than 6000 molecular weight by supported catalysis. In this case, the product from Run No. 3 was used as initiator, but the molecular weight could not be further advanced. It is felt that traces of water in the raw materials/reactor system acted to prevent growth in molecular weight since ethylene oxide was in fact consumed in the reaction. In any case, Table V does demonstrate that high molecular weight poly(oxyethylene)glycols e.g., up to 4000) can be obtained using the supported calcium catalyst of this invention.

EXAMPLE 11

Preparation of Fatty Alcohol Ethoxylates

The catalyst used to prepare this series of $C_{12}/C_{14}$ primary alcohol ethoxylates was Catalyst G. A series of twenty sequential batch preparations were carried out, the target products being the same 6.5 mol ethylene oxide adducts of $C_{12}/C_{14}$ alcohol described in Example 2. The recovered catalyst from each run was extracted with hot toluene, filtered and dried in vacuo before recycling. In this manner, the initial 8.0 gram catalyst charge increased in weight only to 16.8 rams over the course of the experiments. The standard $C_{12}/C_{14}$ alcohol initiator charge was 40.0 in these preparations and the target ethylene oxide feed was 6.5 moles/mole initiator or, more usually, the amount required to reach about a 40–50° C. cloud point non-ionic surfactant product. The reactor used for these experiments was the 600 milliliter stirred autoclave described previously. Table VI below gives pertinent data characterizing the product surfactants and experimental conditions. The reaction rate data of Table VI can be put into proper perspective by noting that the rate for the uncatalyzed reaction of Alfol 1214 with ethylene oxide is about 0.003 grams/minute. FIG. 1 depicts the average ethoxylate distribution for fatty alcohol ethoxylates prepared in this example (supported $CaO/H_2SO_4$) as well as unsupported CaO, unsupported KOH and unsupported $CaO/H_2SO_4$.

TABLE V

|  | RUN NO. | | | |
|---|---|---|---|---|
|  | 1 | 2 | 3 | 4 |
| REACTANTS, g | | | | |
| Catalyst | 3.5[a] | 13.3[b] | 13.5[c] | 10.3[d] |
| PEG-600[e] | 30.0 | 20.0 | 20.62 | — |
| PEG-4083[f] | — | — | — | 41.71 |
| Ethylene Oxide[g] | 189.5 | 199.2 | 136.9 | 41.85 |
| REACTION CONDITIONS | | | | |
| Temperature, °C. | 128–140 | 129–147 | 139–148 | 122–148 |
| Pressure, psig | 11–98 | 10–98 | 10–110 | 8–112 |
| Time, hours | ~33 | ~52 | ~37 | ~40 |
| Prod. Recovery Solvent | Ethylene glycol dimethylether/Acetone | Acetone | Acetone | Acetone |
| PRODUCT CHARACTERIZATION | | | | |
| Product wt., g. | 202.6 | 204.8 | 151.6 | 80.5 |
| Molecular wt. | | | | |
| Theoretical | 4381 | 6563 | 4576 | 8192 |
| Actual | 2432 | 3501 | 4083 | 3985 |
| pH, 5% solution | 4.1 | 3.8 | 3.5 | 3.9 |
| Recovered Cat., g. | 13.3 | 13.5 | 10.4 | 9.7 |
| Viscosity, 50% solution (25° C.), cks | 94.4 | 99.8 | 188.9 | 365.2 |
| Melting Point, °C. | 56–57 | 57.5–59 | 57.5–59 | 59–60 |

[a]Catalyst was Catalyst E; hydroquinone-grafted, acid modified 200–400 mesh Merrifield Resin which was subjected to azeotropic distillation with toluene.
[b]Catalyst was recycled from Run No. 1 after recovery from ethylene glycol dimethylether and acetone media and drying in vacuo to constant weight.
[c]Catalyst was recycled from Run No. 2 after recovery from acetone medium and drying in vacuo.
[d]Catalyst was recycled from Run No. 3 after recovery from acetone medium and drying in vacuo.
[e]A poly(oxyethylene)glycol which contained 0.19% water and had a molecular weight of 599 by hydroxyl number method.
[f]This poly(oxyethylene)glycol initiator was the reaction product from Run No. 3.
[g]Weights shown obtained by actual weighing of gross product and subtracting out weights of initiator and catalyst.

TABLE VI

| | RUN NO. IN SERIES | | | | | | | | | |
|---|---|---|---|---|---|---|---|---|---|---|
| PRODUCT PREPARATION | 1 | 2 | 3 | 4 | 5 | 6 | 7 | 8 | 9 | 10 |
| REACTANT WEIGHTS, g | | | | | | | | | | |
| ALFOL 1214 | 40 | 40 | 40 | 40.2 | 40 | 40 | 40 | 40.1 | 40.1 | 40 |
| CATALYST[a] | 8.0 | 38.5 | 36.2 | 29.3 | 25.9 | 25.65 | 24.7 | 24.2 | 23.9 | 23.3 |
| ETHYLENE OXIDE | 104.5 | 69.0 | 70.0 | 59.7 | 60.6 | 59.1 | 60.4 | 57.7 | 57.6 | 57.3 |
| AGITATOR SPEED, rpm | 610 | 610 | 610 | 610 | 610 | 610 | 610 | 610/490 | 490 | 490 |
| TEMPERATURE, °C. | 140–142 | 140–142 | 139–140 | 140–143 | 140–143 | 140–141 | 140–143 | 145–147 | 150–152 | 155–158 |
| PRESSURE, psig | 10–98 | 10–88 | 10–92 | 10–82 | 10–88 | 10–67 | 10–66 | 10–66 | 10–62 | 10–64 |
| FEED MODE[b] | I/C | I | I | I | I/C | I/C | C | C | C | C |
| REACTION TIME, HRS.[c] | 12.0 | 6.0 | 6.0 | 7.5 | 5 | 5.8 | 7 | 5.7 | 6.25 | 5.75 |
| REACTION RATE, g/min[d] | 0.15 | 0.19 | 0.19 | 0.13 | 0.20 | 0.17 | 0.15 | 0.17 | 0.12 | 0.17 |
| CRUDE NET WEIGHT, g[d] | 149.4 | 145 | 143 | 132.5 | 130 | 125 | 125.5 | 120 | 121 | 119.9 |
| MATERIAL BALANCE, % | 98.0 | 98.6 | 97.8 | 102.6 | 102.4 | 99.7 | 100.3 | 98.4 | 99.5 | 99.4 |
| PRODUCT WEIGHT, g[e] | 100.6 | 112.5 | 108.2 | 101.1 | 101.2 | 97.75 | 101.0 | 99.9 | 98.9 | 96.5 |
| RECOVERED CATALYST, g[f] | 38.05 | 36.2 | 29.4 | 25.9 | 25.65 | 24.7 | 24.2 | 23.9 | 23.3 | 23.7 |
| PRODUCT CHARACTERIZATION | | | | | | | | | | |
| APPEARANCE, 22° C. | SLUSHY SOLID | WAXY SOLID | WAXY SOLID | WAXY SOLID | WAXY SOLID | SLUSHY SOLID | SLUSHY SOLID | SLUSHY SOLID | SLUSHY SOLID | SLUSHY SOLID |
| HYDROXYL NUMBER | 111.6 | 104.8 | 107.6 | 108.4 | 112.1 | 114.1 | 115.7 | 119.5 | 116.1 | 116.9 |
| MOLECULAR WT. (by OH No.) | 502.5 | 535.3 | 521.1 | 517.6 | 500.7 | 491.7 | 485.0 | 469.4 | 483.2 | 480.1 |
| CLOUD POINT, °C. (1% soln.) | 45 | 47 | 47 | 52 | 50 | 45.5 | 47 | 38 | 41.5 | 40 |
| MOLS EO/MOL ALFOL[h] | 6.83 | 7.57 | 7.25 | 7.17 | 6.79 | 6.59 | 6.43 | 6.08 | 6.39 | 6.32 |
| pH, 5% AQ. SOLN. | 6.9 | 4.7 | 4.9 | 6.0 | 6.2 | 5.6 | 5.7 | 7.0 | 6.9 | 7.0 |
| UNREACTED ALCOHOL,[i] WT % | 0.97 | 0.76 | 1.06 | 0.92 | 0.88 | 1.42 | 1.54 | 2.53 | 2.63 | 2.63 |
| ALKALINITY, % AS CaO[j] | 0.0008 | NIL | NIL | NIL | NIL | NIL | NIL | NIL | NIL | NIL |
| ETHER INSOLUBLES, WT %[k] | 12.6 | 18.3 | 26.6 | 12.0 | 9.6 | 6.3 | 9.1 | 6.1 | 5.2 | 5.6 |
| MAJOR COMPONENT, AREA % | E-6 | E-6 | E-6 | E-6 | E-6 | E-6 | E-6 | E-6 | E-6 | E-6 |
| C12-6–C14-7, AREA %[l] | 39.58 | 39.99 | 41.70 | 43.46 | 41.89 | 40.54 | 40.44 | 37.08 | 38.76 | 37.19 |
| C12-5–C14-8, AREA %[l] | 69.19 | 69.86 | 72.69 | 74.03 | 72.12 | 70.28 | 70.06 | 65.18 | 67.20 | 65.04 |
| Ca CONTENTS, ppm[m] | | | | | | | | | | |
| PRODUCT | 135 | — | 140 | — | 35 | — | 16 | — | 60 | — |
| BY-PRODUCT | — | 525 | — | 250 | — | 437 | — | 265 | — | 185 |

| | RUN NO. IN SERIES | | | | | | | | | |
|---|---|---|---|---|---|---|---|---|---|---|
| PRODUCT PREPARATION | 11 | 12 | 13 | 14 | 15 | 16 | 17 | 18 | 19 | 20 |
| REACTANT WEIGHTS, g | | | | | | | | | | |
| ALFOL 1214 | 40 | 40 | 40[g] | 40[g] | 40.1[g] | 40.0 | 40.9 | 40 | 40.1 | 40.0 |
| CATALYST[a] | 23.7 | 22.9 | 22.2 | 21.3 | 20.6 | 18.9 | 18.1 | 17.9 | 17.2 | 16.8 |
| ETHYLENE OXIDE | 57.8 | 60.2 | 58.0 | 64.1 | 71.5 | 57.8 | 58.5 | 58.1 | 58.0 | 58.4 |
| AGITATOR SPEED, rpm | 490 | 389 | 389 | 389 | 389 | 490 | 490 | 490 | 490 | 490 |
| TEMPERATURE, °C. | 130–132 | 137–140 | 139–142 | 149–152 | 139–142 | 140–142 | 140–142 | 139–141 | 140–142 | 140–142 |
| PRESSURE, psig | 10–73 | 10–70 | 10–62 | 10–79 | 10–46 | 10–60 | 10–62 | 10–62 | 10–62 | 10–64 |
| FEED MODE[b] | C | C | C | C/I | C | C | C | C | C | C |
| REACTION TIME, HRS.[c] | 8.3 | 7.75 | 8.25 | 9.25 | 15.0 | 9.65 | 10.5 | 11.0 | 10.0 | 14.0 |
| REACTION RATE, g/min[d] | 0.12 | 0.13 | 0.12 | 0.12 | 0.08 | 0.10 | 0.09 | 0.09 | 0.10 | 0.07 |
| CRUDE NET WEIGHT, g[d] | 125.02 | 122 | 116.6 | 123.7 | 123.6 | 114.7 | 117.3 | 119.3 | 113.8 | 120.2 |
| MATERIAL BALANCE, % | 102.8 | 99.1 | 97.0 | 98.6 | 93.5 | 98.3 | 99.8 | 102.3 | 98.7 | 104.3 |
| PRODUCT WEIGHT, g[e] | 99.1 | 98.6 | 94.4 | 101.2 | 101.6 | 96.4 | 97.9 | 99.5 | 97.9 | 100.7 |
| RECOVERED CATALYST, g[f] | 22.9 | 22.2 | 21.3 | 20.6 | 18.9 | 18.1 | 17.9 | 17.2 | 16.8 | 16.6[e] |
| PRODUCT CHARACTERIZATION | | | | | | | | | | |

TABLE VI-continued

| APPEARANCE, 22° C. | SLUSHY SOLID | SLUSHY SOLID | SLUSHY SOLID | WAXY SOLID | SLUSHY SOLID | SLUSHY SOLID | SLUSHY SOLID | SLUSHY SOLID | SLUSHY SOLID | SLUSHY SOLID |
|---|---|---|---|---|---|---|---|---|---|---|
| HYDROXYL NUMBER | 115.1 | 116.5 | 117.4 | 116.6 | 118.4 | 120.9 | 120.0 | 113.7 | 118.9 | 117.1 |
| MOLECULAR WT. (by OH No.) | 487.5 | 480.9 | 477.7 | 481.2 | 473.7 | 464.1 | 467.4 | 493.5 | 471.9 | 479.1 |
| CLOUD POINT, °C. (1% soln.) | 47 | 44 | 42.5 | 39 | 37 | 38 | 38.5 | 48 | 38.5 | 51 |
| MOLS EO/MOL ALFOL[h] | 6.49 | 6.35 | 6.27 | 6.34 | 6.17 | 5.96 | 6.03 | 6.62 | 6.13 | 6.30 |
| PH, 5% AQ. SOLN. | 6.8 | 7.1 | 6.9 | 7.2 | 6.8 | 6.9 | 6.7 | 7.3 | 6.7 | 6.9 |
| UNREACTED ALCOHOL,[i] WT % | 2.38 | 1.76 | 2.29 | 3.48 | 4.25 | 3.59 | 3.39 | 2.3 | 2.9 | 1.8 |
| ALKALINITY, % AS CaO[j] | NIL | NIL | NIL | NIL | NIL | NIL | NIL | NIL | NIL | NIL |
| ETHER INSOLUBLES, WT %[k] | 8.2 | 8.2 | 6.2 | 14.4 | 16.6 | 6.9 | 5.9 | 4.5 | 5.2 | 6.0 |
| MAJOR COMPONENT, AREA % | E-6 | E-6 | E-6 | E-6 | E-7 | E-6 | E-6 | E-6 | E-6 | E-6 |
| $C_{12-6}$–$C_{14-7}$, AREA %[l] | 40.58 | 39.59 | 39.46 | 37.55 | 35.23 | 37.05 | 36.82 | 39.16 | 37.50 | 40.35 |
| $C_{12-5}$–$C_{14-8}$, AREA %[l] | 69.47 | 68.81 | 67.79 | 65.03 | 61.47 | 64.33 | 64.14 | 67.28 | 65.62 | 68.79 |
| Ca CONTENTS, ppm[m] | | | | | | | | | | |
| PRODUCT | 12 | — | 9 | — | 9 | 9 | 9 | — | 8 | — |
| BY-PRODUCT | — | 150 | — | 120 | — | 115 | — | 117 | — | 116 |

[a]Weight following hot toluene extraction followed by filtration and Rota-Vac drying at 110° C., 5–10 mm Hg pressure.
[b]I = incremental mode of feed; C = continuous mode of feed.
[c]Reaction time shown is to completion of cookout period.
[d]Crude net weight obtained by weighing reactor containing product and subtracting tare weight of reactor.
[e]Actual product obtained by filtration plus product extracted from filter cake.
[f]Weight of catalyst after extraction with hot toluene, filtration and Rota-Vac drying at 110° C./5–10 mm Hg. In some runs, small quantities of catalyst were lost in running cloud point tests.
[f*]Final catalyst weight recovered from run No. 20 was 16.6 g. after ordinary extraction procedure. More vigorous extraction for 5.0 hours with boiling toluene served to remove only 0.25 g. of material. Final Ca analysis was 0.12%, equivalent to 0.24% on original dry catalyst basis.
[g]Alfol 1214 used as pre-dried over molecular sieves.
[h]Alfol 1214 molecular weight of 202 used to calculate this value from hydroxyl molecular weight figure.
[i]By gas chromatography using SP-2100 column with n-decanol internal standard.
[j]By titration with 0.01 N alcoholic HCl in 95/5 MeOH/H₂O using bromothymol blue indicator.
[k]By room temperature extraction of about 25 gram sample with 225 grams of Et₂O followed by filtration and drying of solids in vacuum desiccator overnight.
[l]By gas chromatography using SP-2100 column.
[m]By Inductively Coupled Plasma Emission technique.

EXAMPLE 12

Preparation of Poly(oxyethylene)glycols of about 600 Molecular Weight

Figure 2:
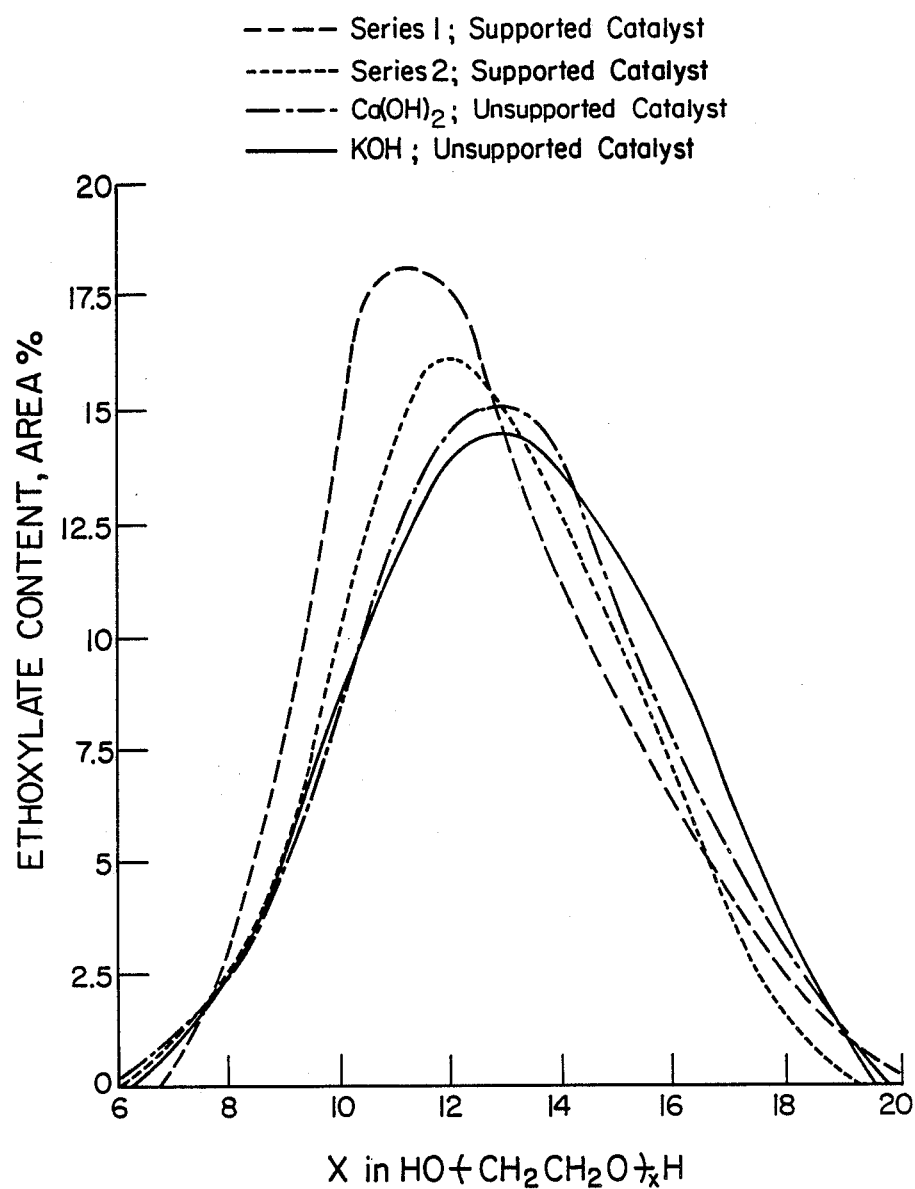
FIG. 2 depicts the average ethoxylate distribution for poly(oxyethylene)glycols prepared in series 1 and series 2 of Example 12 hereinafter (supported CaO) as well as unsupported Ca(OH)$_2$ and unsupported KOH. The average ethoxylate distributions were obtained by averaging (area % values) individual gas chromatography scans.

The catalyst used for the preparation of poly(oxyethylene)glycols was Catalyst H. The unmodified Catalyst H contained 2.95% calcium; it was used (two separate portions) to carryout 2×5 run sequential batch series preparations of poly(oxyethylene)glycols of about 600 molecular weight in a 1-liter stirred autoclave similar to the 300 milliliter and 600 milliliter versions described in previous examples. In these experiments Catalyst H was recovered for recycle by a centrifugation/decantation procedure which provided a "wet" form for recycle. For seven of these ten runs, the standard charge of diethylene glycol initiator was 35.0 grams; for the last three runs, this charge was 32.0 grams. The target feed for ethylene oxide was about 163 grams, the theoretical quantity necessary to advance the diethylene glycol charge to a polymer of about 600 molecular weight. Molecular weights attained were invariably somewhat below theoretical; this was undoubtedly due to the present of poly(oxyethylene)glycols absorbed on the catalyst, effectively increasing the quantity of initiating species present. Experimental details and product characterization data are summarized in Tables VII and VIII below. FIG. 2 depicts the average ethoxylate distribution for poly(oxyethylene)glycols prepared in series 1 and series 2 of this example (supported CaO) as well as unsupported $Ca(OH)_2$ and unsupported KOH.

TABLE VII

| RUN SERIES | ONE | | | | |
|---|---|---|---|---|---|
| RUN NO. IN SERIES | 1 | 2 | 3 | 4 | 5 |
| Preparation | | | | | |
| Temperature, °C.,[a] | 140–160 | 140–160 | 140–150 | 140–175 | 140–160 |
| Pressure, psig[b] | 20–98 | 20–98 | 20–104 | 12–104 | 18–104 |
| Reactants Weights, g. | | | | | |
| Diethylene Glycol | 35.0 | 35.0 | 35.0 | 35.0 | 35.0 |
| Catalyst[d] | 4.0 | 9.62 | 10.95 | 12.0 | 14.01 |
| Ethylene Oxide[c] | 163.5 | 173.2 | 163.1 | 175.1 | 166.8 |
| Reaction Time, Hrs. (approx.) | 15 | 17 | 23.0 | 34 | 57 |
| Product Weight, g. | 197.1 | 201.3 | 198.2 | 207.9 | 209.0 |
| Material Balance % | 97.3 | 92.4 | 94.8 | 93.6 | 96.8 |
| Characterization | | | | | |
| Appearance, 25° C. | v. slushy liq. | hazy liq. | hazy liq. | hazy liq. | slushy liq. |
| Molecular Weight, by OH No. | 556.2 | 549.7 | 529.6 | 527.3 | 532.2 |
| Alkalinity, as CaO, %[e] | 0.0423 | 0.0058 | 0.0031 | 0.0017 | 0.0012 |
| pH, 5% Aqueous Solution | 10.06 | 8.35 | 7.121 | 6.92 | 6.80 |
| Viscosity, CKS @ 25° C., 50% Aqueous Sol'n. | 13.1 | 12.7 | 12.5 | 13.0 | 13.1 |
| Absolute Ethanol Insolubles, %[g] | 2.8 | 4.2 | 2.9 | 4.6 | 1.7 |
| Ethoxylate Distribution, Area %[f] | | | | | |
| Pentaethylene Glycol | — | 0.03 | 0.04 | — | — |
| Hexaethylene Glycol | <0.02 | 0.06 | 0.05 | <0.05 | 0.1 |
| Heptaethylene Glycol | 0.04 | 0.63 | 0.43 | 0.26 | 0.77 |
| Octaethylene Glycol | 1.02 | 3.37 | 3.71 | 1.91 | 3.93 |
| Nonaethylene Glycol | 7.15 | 8.5 | 9.55 | 5.09 | 9.25 |
| Decaethylene Glycol | 15.71 | 15.02 | 16.04 | 13.18 | 14.45 |
| Undecaethylene Glycol | 21.55 | 18.83 | 19.33 | 15.30 | 17.44 |
| Dodecaethylene Glycol | 20.94 | 18.03 | 18.04 | 15.11 | 16.94 |
| Tridecaethylene Glycol | 15.61 | 13.94 | 13.62 | 13.11 | 13.73 |
| Tetradecaethylene Glycol | 9.48 | 9.29 | 8.75 | 10.38 | 9.82 |
| Pentadecaethylene Glycol | 4.89 | 5.68 | 5.25 | 8.11 | 6.55 |
| Hexadecaethylene Glycol | 2.33 | 3.78 | 3.18 | 5.35 | 4.75 |
| Heptadecaethylene Glycol | 0.89 | 1.77 | 1.35 | 2.36 | 2.04 |
| Octadecaethylene Glycol | 0.31 | 0.63 | 0.52 | 0.53 | 0.28 |
| Nonadecaethylene Glycol | <0.1 | 0.27 | 0.17 | — | 0.04 |

[a]Range experienced; target temperature was 104° C.; excursions were principally of mechanical malfunction origin.
[b]Ranges shown do not include extreme values experienced during temperature excursions due to mechanical problems.
[c]Weight indicated by tank readings of weight loss corrected by occasional actual weight checks.
[d]Original catalyst change was 4.0 grams; higher weights in subsequent runs reflect presence of residual products build-up on resin.
[e]By titration with 0.01N alcoholic HCl in CELLOSOLVE using bromothymol blue indicator.
[f]Obtained with SP-2100 column using Regisil ® - derivatized sample.
[g]Extraction of 25 grams with absolute ethanol at room temperature followed by filtration evaporation of filtrate.

TABLE VIII

| RUN SERIES | TWO | | | | |
|---|---|---|---|---|---|
| RUN NO. IN SERIES | 1 | 2 | 3 | 4 | 5 |
| Preparation | | | | | |
| Temperature, °C.,[a] | 140–170 | 140–165 | 140–162[g,h] | 140–190[g,h] | 140–161[h,i] |
| Pressure, psig[b] | 20–104 | 10–104 | 12–108 | 8–112 | 9–120 |
| Reactants Weights, g. | | | | | |
| Diethylene Glycol | 35.0 | 35.0 | 32.0 | 32.0 | 32.0 |
| Catalyst[d] | 4.0 | 10.22 | 14.4 | 10.65 | 12.43 |

TABLE VIII-continued

| RUN SERIES | TWO | | | | |
|---|---|---|---|---|---|
| RUN NO. IN SERIES | 1 | 2 | 3 | 4 | 5 |
| Ethylene Oxide[c] | 163.6 | 165.0 | 167.6 | 173.3 | 167.4 |
| Reaction Time, Hrs. (approx.) | 20 | 24 | 26 | 62 | >60 |
| Product Weight, g. | 201.5 | 207.2 | 212.45 | 212.27 | 208.1 |
| Material Balance % | 99.5 | 98.6 | 99.3 | 98.3 | 98.2 |
| Characterization | | | | | |
| Appearance, 25° C. | Slushy Solid | Hazy Liq. | Waxy Liq. | Slushy Solid | Hazy Liquid |
| Molecular Weight, by OH No. | 568.4 | 558.3 | 619.1 | 550.6 | 531.9 |
| Alkalinity, as CaO, %[e] | 0.0564 | 0.0074 | 0.0025 | 0.0008 | 0.0006 |
| pH, 5% Aqueous Solution | 10.3 | 9.07 | 7.1 | 7.3 | 7.1 |
| Viscosity, CKS @ 25° C., 50% Aqueous Sol'n. | 14.3 | 13.7 | 15.1 | 15.0 | 14.5 |
| Absolute Ethanol Insolubles, %[j] | 6.2 | 4.0 | 1.5 | 4.0 | 2.2 |
| Ethoxylate Distribution, Area %[f] | | | | | |
| Pentaethylene Glycol | 0.21 | 0.05 | — | — | 0.02 |
| Hexaethylene Glycol | 0.43 | 0.47 | — | 0.05 | 0.03 |
| Heptaethylene Glycol | 0.77 | 0.93 | 0.30 | 0.84 | 1.25 |
| Octaethylene Glycol | 2.65 | 2.80 | 1.99 | 3.11 | 3.11 |
| Nonaethylene Glycol | 4.93 | 6.44 | 4.46 | 6.05 | 6.03 |
| Decaethylene Glycol | 12.11 | 11.06 | 8.02 | 9.79 | 9.5 |
| Undecaethylene Glycol | 18.45 | 14.76 | 11.97 | 13.27 | 12.65 |
| Dodecaethylene Glycol | 20.12 | 16.06 | 14.80 | 15.14 | 14.51 |
| Tridecaethylene Glycol | 16.76 | 14.98 | 15.57 | 15.02 | 14.46 |
| Tetradecaethylene Glycol | 11.37 | 12.30 | 14.73 | 13.46 | 12.67 |
| Pentadecaethylene Glycol | 6.97 | 9.49 | 13.03 | 11.12 | 9.86 |
| Hexadecaethylene Glycol | 3.90 | 6.03 | 9.36 | 7.78 | 7.04 |
| Heptadecaethylene Glycol | 1.58 | 2.91 | 4.80 | 3.84 | 4.86 |
| Octadecaethylene Glycol | 0.38 | 0.59 | 0.88 | 0.53 | 2.94 |
| Nonadecaethylene Glycol | 0.10 | — | — | — | 0.84 |

[a]Range experienced; target temperature was 104° C.; temperature excursions were principally of mechanical modification origin.
[b]Ranges shown do not include extreme values experienced during temperature excursions due to mechanical problems.
[c]Weight indicated by tank reading of weight loss corrected by occasional actual weight checks.
[d]Original catalyst change was 4.0 grams; higher weights in subsequent runs reflect presence of residual products build-up on resin.
[e]By titration with 0.01N alcoholic HCl in CELLOSOLVE using bromothymol blue indicator.
[f]Obtained with SP-2100 column using Regisil ® - derivatized examples.
[g]Major equipment malfunctions during these runs; temperature exceeded 200° C. at times, especially in case of run number 4.
[h]An internal cooling coil was added part way through run 3 and used thereafter to improve temperature control.
[i]Catalyst activity was low; catalyst damage was probably sustained during run #4, or runs 3 and 4.
[j]Extraction of 25 grams with 250 grams absolute ethanol at room temperature.

EXAMPLE 13

Preparation of Poly(oxyethylene)glycols of about 300 Molecular Weight

The catalyst for this series of 5 sequential batch preparations was Catalyst J. The poly(oxyethylene)glycol preparations with Catalyst J were carried out in a 1.5 gallon circulated loop type autoclave equipped to automatically feed ethylene oxide as needed to maintain 60 psig. The starter for these runs was diethylene glycol (DEG); a typical starter charge was about 500 grams while a typical target quantity of ethylene oxide was about 915 grams. The catalyst recovery/recycle procedure used in this series involved filtering the crude reaction product, slurring the moist recovered catalyst in toluene at 80-90° C., refiltering and drying in vacuo at 100° C./5 mm Hg. The original catalyst charge for the series of preparations was 12.0 grams; the final catalyst weight after completion of the series was about 21 grams. Experimental details and pertinent product characterization data for this series of preparations are given in Table IX below.

TABLE IX

| | RUN NO. IN SERIES | | | | |
|---|---|---|---|---|---|
| | 1 | 2 | 3 | 4 | 5 |
| Preparative Conditions | | | | | |
| Temperature, °C. | 138-142 | 140-142 | 140-142 | 140-143 | 139-141 |
| Pressure, psig | 62.5-64 | 61-68 | 60-67 | 62-66 | 61-74 |
| Reaction Time, Hrs. | ~4 | ~18 | ~32 | ~43 | ~32 |
| Reactants/Weights | | | | | |
| Diethylene Glycol | 497 | 503 | 500 | 500 | 501 |
| Ethlyene Oxide | 908 | 914 | 913 | 924 | 912 |
| Catalyst | 12.0 | 22.8 | 25.1 | 21.8 | 22.0 |
| Product Weight, g. | 1339 | 1368 | 1360 | 1345 | 1366 |
| Material Balance % | 94.5 | 95.0 | 94.6 | 93.0 | 95.3 |
| Product Characterization | | | | | |
| Molecular Weight (by OH No.) | 292.1 | 300.5 | 286.7 | 295.0 | 302.6 |
| Alkalinity, meqs/g. | 0.0129 | 0.0018 | 0.0007 | 0.0001 | 0.0007 |
| pH, 5% Aqueous Sol'n | 9.95 | 8.60 | 7.12 | 6.41 | 6.45 |
| Mols EO/Mol. DEG. | 4.23 | 4.43 | 4.11 | 4.30 | 4.47 |
| Ethoxylate Distribution, Area % | | | | | |

TABLE IX-continued

|  | RUN NO. IN SERIES | | | | |
| --- | --- | --- | --- | --- | --- |
|  | 1 | 2 | 3 | 4 | 5 |
| Diethylene Glycol | — | — | — | — | — |
| Triethylene Glycol | 0.31 | 0.36 | 0.98 | 1.46 | 0.78 |
| Tetraethylene Glycol | 9.11 | 9.26 | 10.71 | 10.70 | 9.56 |
| Pentaethylene Glycol | 20.61 | 20.61 | 20.84 | 19.69 | 18.68 |
| Hexaethylene Glycol | 25.32 | 24.78 | 23.92 | 22.83 | 22.59 |
| Heptaethylene Glycol | 21.32 | 21.04 | 20.15 | 19.90 | 20.45 |
| Octaethylene Glycol | 13.58 | 13.58 | 13.13 | 13.56 | 14.45 |
| Nonaethylene Glycol | 6.76 | 6.98 | 6.85 | 7.47 | 8.22 |
| Decaethylene Glycol | 2.60 | 2.85 | 2.86 | 3.39 | 3.84 |
| Undecaethylene Glycol | 0.40 | 0.54 | 0.55 | 1.00 | 1.30 |
| Dodecaethylene Glycol | — | — | — | — | 0.07 |

EXAMPLE 14

Part A. Preparation of Poly(oxyethylene)glycols of about 300 Molecular Weight

The catalyst for these two preparations of poly(oxyethylene)glycols of about 300 molecular weight was Catalyst K. The reactor for these preparations was a 1-liter stirred autoclave equipped with an automatic ethylene oxide feed system wherein a motor valve controlled the feed of ethylene oxide to maintain about 60 psig pressure.

The temperature at which these runs were made was 140–148° C.; the initiator used was ethylene glycol For the first of the two preparations, 80.0 grams of ethylene glycol was charged along with 8.0 grams of Catalyst K. The amount of ethylene oxide fed was 308.2 grams; the reaction time was five hours. For the second preparation, the recovered catalyst (moist, 14.4 grams wet) was charged along with 80.0 grams of ethylene glycol and 310 grams of ethylene oxide was fed according to weight loss indicated for the oxide feed tank. The reaction time for this run was about 11 hours. The properties of the poly(oxyethylene)glycol products are given in Table X below.

TABLE X

|  | Run No. In Series | |
| --- | --- | --- |
|  | 1 | 2 |
| Molecular Weight (by OH #) | 284.5 | 258.7 |
| Mols EO/Mol EG | 5.06 | 4.47 |
| pH, 5% Aqueous Solution | 9.0 | 8.75 |
| Alkalinity, Meqs/g. (by titration) | 0.0009 | 0.0007 |
| Calcium content, ppm (by ICPE) | 26 | 27 |
| Color | Straw | Straw |
| Major Component, by GC | Hexaethylene Glycol | Hexaethylene Glycol |
| Conc. of Major Component, GC Area % | 20.2 | 20.7 |

Part B. Preparation of Fatty Alcohol Ethoxylates

The catalyst for these four preparations of $C_{12}/C_{14}$ primary alcohol ethoxylates was Catalyst L. The exchanged reaction product was stripped free of most of the excess Alfol 1214 to leave the catalyst as a concentrated slurry in Alfol 1214 (89 grams total weight). The 89.0 grams of slurry was used as charge for the first ethoxylation in the series of five. For each of the subsequent runs, the catalyst was material recovered (by filtration) from the previous run and the Alfol 1214 charge was 40.0 grams. The runs were made in the 600 milliliter stirred autoclave described previously. Typical conditions were about 140° C. temperature; about 60–80 psig pressure; ethylene oxide feed was by manual means, increments being fed as convenient to keep pressure within the desired range. Pertinent data on these four ethoxylations is summarized in Table XI below; the first preparation in the series afforded atypical product because major mechanical problems were encountered during the run.

TABLE XI

|  | Run No. in Series | | | |
| --- | --- | --- | --- | --- |
|  | 1 | 2 | 3 | 4 |
| Mols EO/Mol Alfol 1214 | 4.25 | 6.22 | 6.02 | 6.25 |
| Molecular Weight (by OH No.) | 389.0 | 475.7 | 467.2 | 477.1 |
| Cloud Point, °C. (1% Solution) | ~25 | 42 | 42 | 50 |
| pH, 5% Aqueous Solution | 8.3 | 7.4 | 7.35 | 7.3 |
| Alkalinity, meq/g. | n.d. | 0.0005 | 0.0004 | 0.001 |

EXAMPLE 15

Preparation of Poly(oxyethylene)glycols of about 300 Molecular Weight

The catalysts for these two series of poly(oxyethylene)glycol preparations were Catalyst M and Catalyst N. Both unmodified Catalyst M and acid-modified Catalyst N were used to conduct 4-run sequential batch preparations of poly(oxyethylene)glycol products. In both series of preparations the reactor was the 600 milliliter stirred autoclave described previously and the initial catalyst charge was 8.5 grams. Diethylene glycol was employed as the initiator, 30.0 grams being the standard charge for each run. The target quantity of ethylene oxide feed was about 58.5 grams; temperature and pressure used were 140° C. and 60 psig, respectively. The procedure used for recovering/recycling the catalysts was to filter the crude reaction product, slurry the recovered catalyst in hot toluene (80–90° C. two hours), refilter, and dry the solid in vacuo at ambient temperature. The portion of the liquid product recovered each time from slurrying the wet catalyst in toluene invariably had the same composition (by gas chromatography) as the main portion of the product obtained from the initial filtration. Tables XII and XIII below contain pertinent data on these two series of poly(oxyethylene)glycol preparations; Table XII covers the experiments carried out with unmodified Catalyst M and Table XIII the experiments with acid-modified Catalyst N.

TABLE XII

|  | Run No. In Series | | | |
| --- | --- | --- | --- | --- |
|  | 1 | 2 | 3 | 4 |
| Molecular Weight (by OH No.) | 340.5 | 332.9 | 299.3 | 299.3 |
| Alkalinity, meqs/g. | 0.009 | 0.016 | 0.010 | 0.0027 |
| pH, 5% Aqueous Solution | 9.7 | 10.05 | 9.6 | 8.0 |
| Reaction Time, hours | 5.0 | 3.1 | 5.0 | 14.0 |

TABLE XII-continued

| | Run No. In Series | | | |
|---|---|---|---|---|
| | 1 | 2 | 3 | 4 |
| Ethoxylate Distribution, Area % | | | | |
| Diethylene Glycol | — | — | — | — |
| Triethylene Glycol | — | — | 0.29 | 0.31 |
| Tetraethylene Glycol | 3.03 | 4.18 | 9.44 | 10.22 |
| Pentaethylene Glycol | 10.82 | 12.86 | 21.22 | 21.80 |
| Hexaethylene Glycol | 18.97 | 20.66 | 25.16 | 24.67 |
| Heptaethylene Glycol | 22.38 | 22.45 | 20.59 | 19.71 |
| Octaethylene Glycol | 19.50 | 18.16 | 12.86 | 12.29 |
| Nonaethylene Glycol | 13.35 | 11.67 | 6.59 | 6.39 |
| Decaethylene Glycol | 7.47 | 6.25 | 2.91 | 2.96 |
| Undecaethylene Glycol | 3.44 | 2.85 | 0.95 | 1.27 |
| Dodecaethylene Glycol | 1.05 | 0.92 | — | 0.39 |

TABLE XIII

| | Run No. In Series | | | |
|---|---|---|---|---|
| | 1 | 2 | 3 | 4 |
| Molecular Weight, (by OH No.) | 371.0$^a$ | 294.5 | 312.7 | 323.6$^a$ |
| Alkalinity, meqs/g. | 0.0173 | 0.0029 | 0.001 | 0.0009 |
| pH, 5% Aqueous Solution | 10.01 | 8.50 | 7.05 | 7.36 |
| Reaction Time, Hours | 3.4 | 5.75 | 8.75 | 9.0 |

$^a$Unintentional overfeed of ethylene oxide accounts for high molecular weight.

EXAMPLE 16

Preparation of Poly(oxyethylene)glycols of about 200 Molecular Weight

The catalyst used for making this series o 8 sequential runs was Catalyst P. The poly(oxyethylene)glycol preparation carried-out using modified Catalyst P comprised a series of 8 sequential batch runs in the 600 milliliter stirred autoclave described previously. The initiator for these runs was ethylene glycol; the standard initiator charge was 31.0 grams and the target quantity of ethylene oxide was 69.8 grams in each run. Catalyst P was used in an initial quantity of 7.5 grams; subsequent runs employed recycled catalyst obtained by filtering the reaction product, slurrying the recovered catalyst in hot toluene, refiltering, and finally drying the recovered solid catalyst in vacuo at 85° C./~5 mm Hg pressure. Following this procedure, the weight of dried catalyst recovered after the 8th and final batch run was 7.7 grams; the calcium and sulfur contents were 0.18 and 0.1%, respectively. Table XIV below contains pertinent data on characterization of the poly(oxyethylene)glycol products made in this experiment.

Although the invention has been illustrated by the preceding examples, it is not to be construed as being limited thereby; but rather, the invention encompasses the generic area as hereinbefore disclosed. Various modifications and embodiments can be made without departing from the spirit and scope thereof.

We claim:
1. A method for providing an alkoxylation catalyst comprising:
   (a) preparing a catalyst precursor by reacting an organic polymer which has a crosslinked and microporous, macroporous or physically expanded structure with a carbocyclic or heterocyclic compound;
   (b) solubilizing, at least partially, calcium oxide, calcium hydroxide, or mixtures thereof, by mixing any of them with an activator having the formula

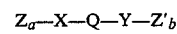

$$Z_a-X-Q-Y-Z'_b$$

wherein X and Y are the same or different electronegative, hetero-atoms selected from the group consisting of oxygen, nitrogen, sulfur and phosphorus; a and b are the same or different integers satisfying the valency requirements of X and Y; Q is an organic radical which is electropositive or essentially neutral relative as to X and/or Y; Z and Z' are the same or different and are either hydrogen or an organic radical which does not prevent said solubilizing, thereby forming a calcium-containing, composition which has titratable alkalinity; and
   (c) reacting the catalyst precursor with the calcium-containing composition under effective reaction conditions to chemically bond the calcium atom to the polymer through a carbocyclic or heterocyclic linkage.

2. The method of claim 1 wherein the organic polymer is a polystyrenic polymer or a phenolic polymer.

3. The method of claim 1 wherein the organic polymer is a copolymer of styrene and divinyl benzene.

4. The method of claim 1 wherein the organic polymer is a chloromethylated styrene/divinyl benzene polymer.

5. The method of claim 1 wherein the carbocyclic or heterocyclic compound is of the monocyclic or polycyclic type.

6. The method of claim 1 wherein the carbocyclic or heterocyclic compound provides an aryloxy or arylthio functional group having a pKa in the range of 7–13.

7. The method of claim 1 wherein the activator has the formula:

TABLE XIV

| | Run No. In Series | | | | | | | |
|---|---|---|---|---|---|---|---|---|
| | 1 | 2 | 3 | 4 | 5 | 6 | 7 | 8 |
| Molecular Wt. by OH No. | 199.2 | 201.9 | 206.3 | 196.6 | 188.7 | 194.1 | 194.7 | 199.4 |
| Alkalinity, meqs/g. | 0.0074 | 0.0038 | 0.0019 | 0.0008 | 0.0004 | 0.0005 | 0.0006 | 0.0002 |
| pH, 5% Aqueous Sol'n | 8.30 | 7.33 | 7.30 | 7.42 | 6.96 | 7.09 | 7.11 | 6.50 |
| Reaction Time, hours | 4.0 | 6.5 | 11.75 | 15.25 | 12.0 | 11.75 | 12.25 | 16.25 |
| Calcium Content in Product, ppm | 143 | 33 | 19 | 14 | 2.8 | 2.2 | 1.4 | 0.4 |
| Ethoxylate Distribution, GC Area % | | | | | | | | |
| Ethylene Glycol | 0.44 | 0.13 | — | 0.14 | 0.99 | 0.82 | 1.16 | 2.24 |
| Diethylene Glycol | 0.73 | 0.21 | 0.10 | 0.47 | 6.75 | 4.82 | 5.75 | 8.12 |
| Triethylene Glycol | 26.88 | 23.75 | 21.84 | 30.45 | 39.37 | 29.27 | 27.60 | 25.33 |
| Tetraethylene Glycol | 43.30 | 43.17 | 44.11 | 41.09 | 32.21 | 31.83 | 30.37 | 28.12 |
| Pentaethylene Glycol | 20.89 | 22.53 | 23.57 | 19.09 | 14.23 | 19.46 | 19.58 | 19.61 |
| Hexaethylene Glycol | 6.13 | 7.28 | 7.71 | 6.40 | 5.06 | 9.17 | 9.82 | 10.55 |
| Heptaethylene Glycol | 1.21 | 1.87 | 2.04 | 1.86 | 1.39 | 3.50 | 4.03 | 4.56 |
| Octaethylene Glycol | 0.05 | 0.45 | 0.51 | 0.47 | — | 0.95 | 1.36 | 1.48 |
| Nonaethylene Glycol | — | — | — | — | — | — | 0.14 | — |

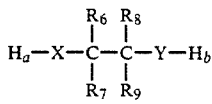

wherein $R_6$, $R_7$, $R_8$ and $R_9$ are the same or different and are selected from the group consisting of hydrogen and lower alkyl or alkylene groups of one to four carbon atoms.

8. The method of claim 1 wherein the activator is ethylene glycol.

9. The method of claim 1 wherein the activator is 2-ethoxyethanol.

10. The method of claim 1 comprising the additional step of reacting the alkoxylation catalyst with an alcohol under conditions at which an alcohol exchange reaction occurs with the alkoxylation catalyst, thereby producing a corresponding alcohol derivative.

11. The method of claim 10 wherein the alcohol is n-dodecanol.

12. The method of claim 10 wherein the alcohol is a mixture of $C_{12}$ and $C_{14}$ alcohols.

13. The method of claim 1 comprising the additional step of removing some or all activator which is not bound to calcium.

14. A method of claim 1 comprising the additional step of adding a sufficient amount of a polyvalent, oxy acid or a metal salt thereof to neutralize a portion of the titratable alkalinity sufficient to enhance the selectivity of the catalyst.

15. A method of claim 10 comprising the additional step of adding a sufficient amount of a polyvalent, oxy-acid or a metal salt thereof to neutralize a portion of the titratable alkalinity sufficient to enhance the selectivity of the catalyst.

16. The method of claim 14 wherein the oxy-acid is sulfuric acid.

17. The method of claim 16 wherein about 25 to about 75% of the titratable alkalinity is neutralized.

18. The method of claim 16 wherein about 40 to about 60% of the titratable alkalinity is neutralized.

19. An alkoxylation catalyst having the formula:

$$R_1—R_2—X_1—Ca—X_2—R_3$$

wherein:
$R_1$ is an organic polymeric residue which has a cross-linked and microporous, macroporous or physically expanded structure;
$R_2$ is a carbocyclic or heterocyclic residue;
$X_1$ and $X_2$ are independently oxygen or sulfur; and
$R_3$ is hydrogen or an organic residue of an organic compound having at least one active hydrogen.

20. The alkoxylation catalyst of claim 19 in which said catalyst is reacted with an alcohol under conditions at which an alcohol exchange reaction occurs with the catalyst, thereby producing a corresponding alcohol derivative.

21. The alkoxylation catalyst of claim 19 in which a sufficient amount of a polyvalent, oxy-acid or a metal salt thereof is reacted with said catalyst to neutralize a portion of the titratable alkalinity sufficient to enhance the selectivity of the catalyst.

22. An alkoxylation catalyst prepared by the method of claim 1.

23. An alkoxylation catalyst prepared by the method of claim 10.

24. An alkoxylation catalyst prepared by the method of claim 14.

25. An alkoxylation catalyst prepared by the method of claim 15.

* * * * *